(12) United States Patent
Takahashi et al.

(10) Patent No.: US 8,618,701 B2
(45) Date of Patent: Dec. 31, 2013

(54) ACTUATOR AND ELECTRIC TOOTHBRUSH USING ACTUATOR

(75) Inventors: Yuki Takahashi, Tokyo (JP); Shigenori Inamoto, Tokyo (JP); Yasutaka Kitamura, Tokyo (JP); Kensuke Yamada, Tokyo (JP)

(73) Assignee: Mitsumi Electric Co., Ltd., Tokyo (JP)

(*) Notice: Subject to any disclaimer, the term of this patent is extended or adjusted under 35 U.S.C. 154(b) by 272 days.

(21) Appl. No.: 13/126,681

(22) PCT Filed: Oct. 29, 2009

(86) PCT No.: PCT/JP2009/005760
§ 371 (c)(1),
(2), (4) Date: Apr. 28, 2011

(87) PCT Pub. No.: WO2010/050224
PCT Pub. Date: May 6, 2010

(65) Prior Publication Data
US 2011/0203061 A1    Aug. 25, 2011

(30) Foreign Application Priority Data

Oct. 31, 2008  (JP) ................................. 2008-282360
Oct. 31, 2008  (JP) ................................. 2008-282361

(51) Int. Cl.
*H02K 33/00* (2006.01)
(52) U.S. Cl.
USPC ......................................... 310/15; 310/12.14
(58) Field of Classification Search
USPC .................. 310/12.14, 14, 15, 23, 30, 34, 36; 15/22.1, 22.2, 22.4, 23, 28
See application file for complete search history.

(56) References Cited

U.S. PATENT DOCUMENTS

| 5,189,751 | A | 3/1993 | Giuliani et al. |
| 8,327,488 | B2* | 12/2012 | Takahashi et al. ............. 15/22.1 |
| 2003/0204924 | A1 | 11/2003 | Grez et al. |
| 2004/0010871 | A1 | 1/2004 | Nishinaka et al. |
| 2005/0200207 | A1* | 9/2005 | Hasegawa et al. .............. 310/10 |

(Continued)

FOREIGN PATENT DOCUMENTS

| CN | 1432346 A | 7/2003 |
| JP | 07-505069 A | 6/1995 |

(Continued)

OTHER PUBLICATIONS

Notice Of Reasons For Rejection For Japanese Patent Application 2008-282361, Japanese Patent Office, May 15, 2012.

*Primary Examiner* — Thanh Lam
(74) *Attorney, Agent, or Firm* — Washida & Associates

(57) ABSTRACT

Disclosed is an actuator that generates the reciprocating rotational motion of an electric toothbrush or similar without employing a drive transmission mechanism as a separate entity from a drive source. An actuator (100) includes a fixed body (110) comprising an outer yoke (140) having inner wall planes that respectively oppose the magnetic pole planes of unlike poles of a magnet (150) with a predetermined gap therebetween. A coil (122) is arranged to encircle the magnet (150) between the magnetic pole planes of the unlike poles of the magnet (150) and the inner wall planes of the outer yoke (140) that respectively oppose the magnetic pole planes of the unlike poles, and this coil (122) is movably supported as a movable body (120) by way of an elastic member (130) fastened to the fixed body (110). The reciprocating rotational motion of the movable body (120) is afforded by the supply of an alternating current of a frequency approximately equivalent to the resonant frequency of the movable body (120) from an alternating current supply (180) to the coil (122).

15 Claims, 27 Drawing Sheets

(56) References Cited

U.S. PATENT DOCUMENTS

| | | |
|---|---|---|
| 2005/0235438 A1 | 10/2005 | Motohashi et al. |
| 2006/0066154 A1 | 3/2006 | Ogino et al. |
| 2006/0255665 A1* | 11/2006 | Kraus et al. .................... 310/36 |
| 2011/0214239 A1* | 9/2011 | Kagami et al. ................. 15/22.1 |

FOREIGN PATENT DOCUMENTS

| | | | |
|---|---|---|---|
| JP | 08-065990 | A | 3/1996 |
| JP | 3243529 | B | 1/2002 |
| JP | 2002-078310 | A | 3/2002 |
| JP | 2005-099063 | A | 4/2005 |
| JP | 2005-525067 | T | 8/2005 |
| JP | 2006-101650 | A | 4/2006 |
| JP | 2007-014130 | A | 1/2007 |
| JP | 2007-020589 | A | 2/2007 |
| JP | 2007-082272 | A | 3/2007 |
| JP | 2008-058660 | A | 3/2008 |
| WO | 93/15628 | A | 8/1993 |
| WO | 02-48022 | A | 6/2002 |

* cited by examiner

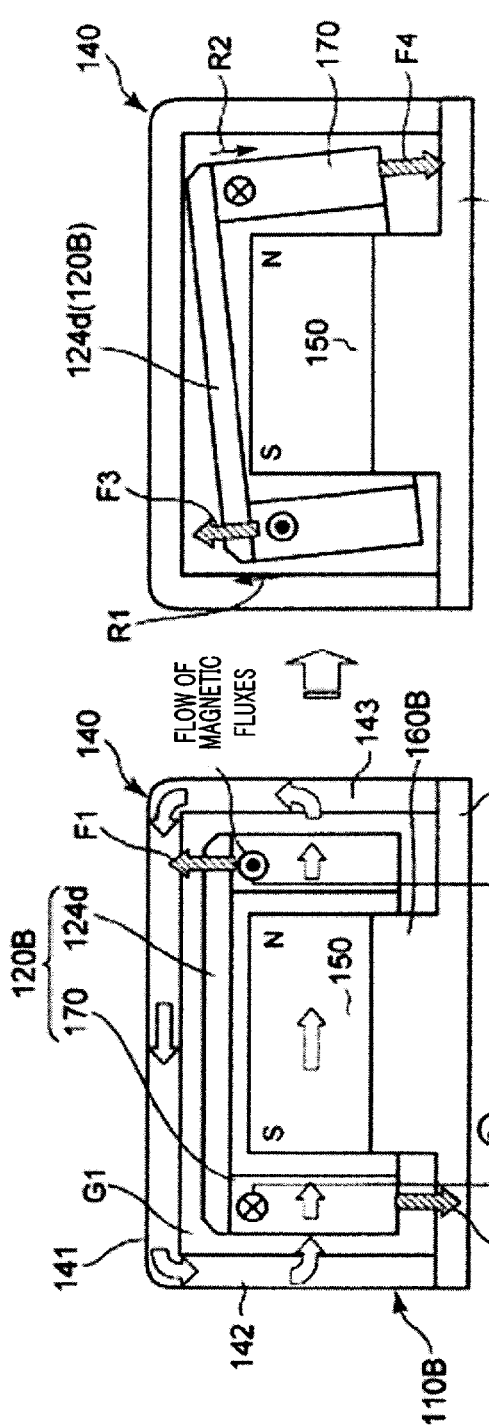
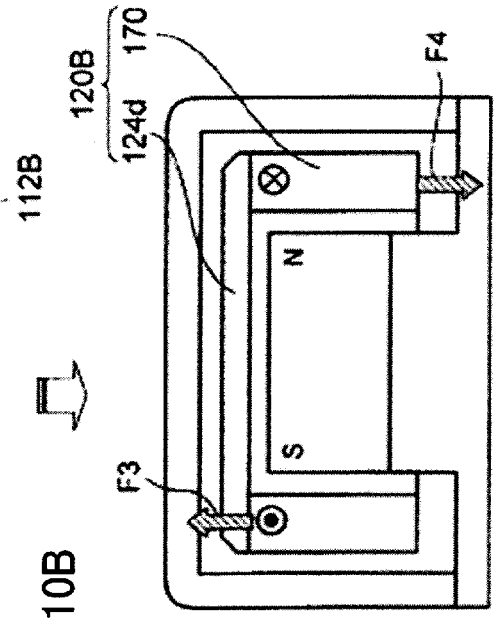
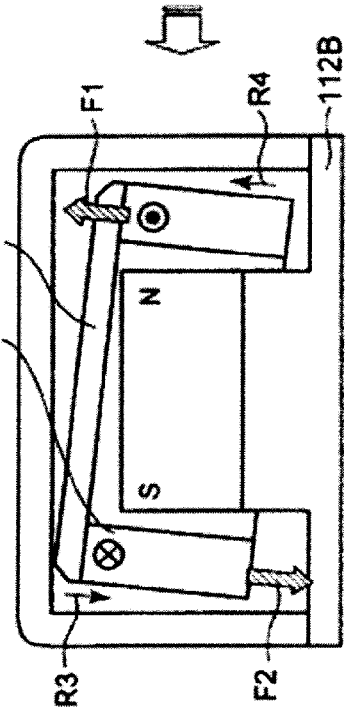
FIG.10A
FIG.10B
FIG.10C
FIG.10D

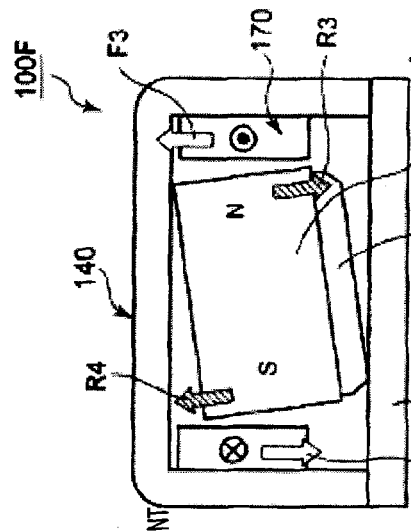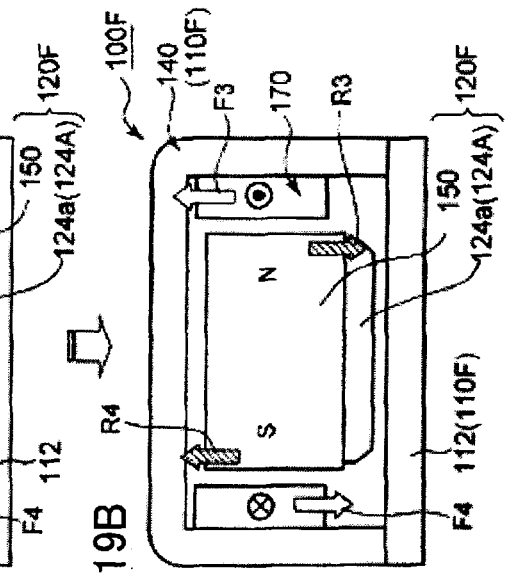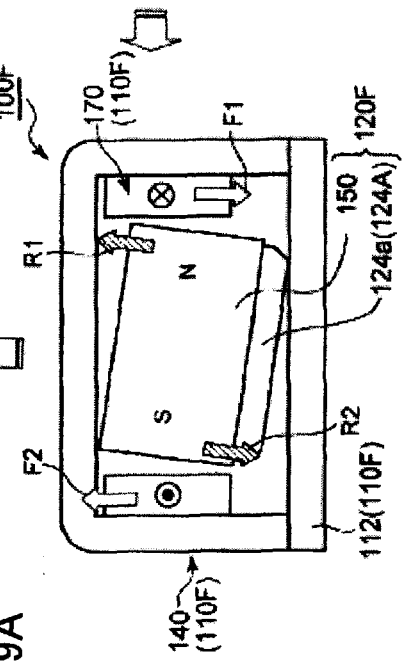
FIG.19A
FIG.19B
FIG.19C
FIG.19D

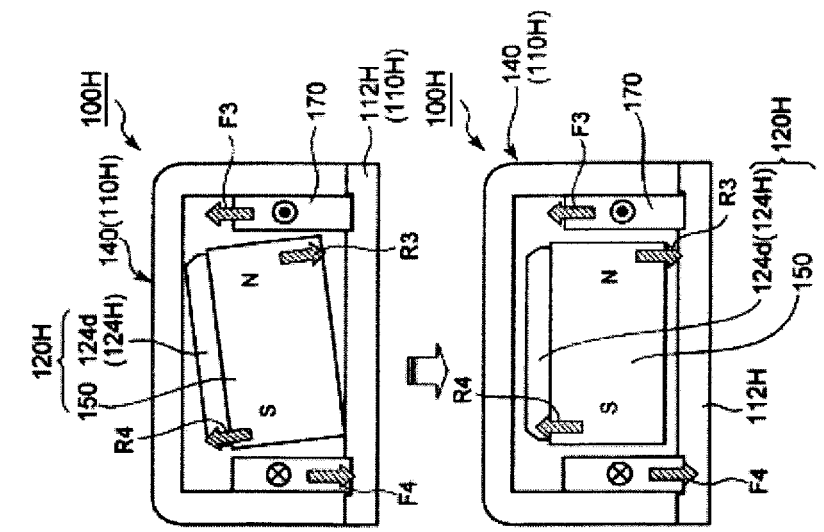
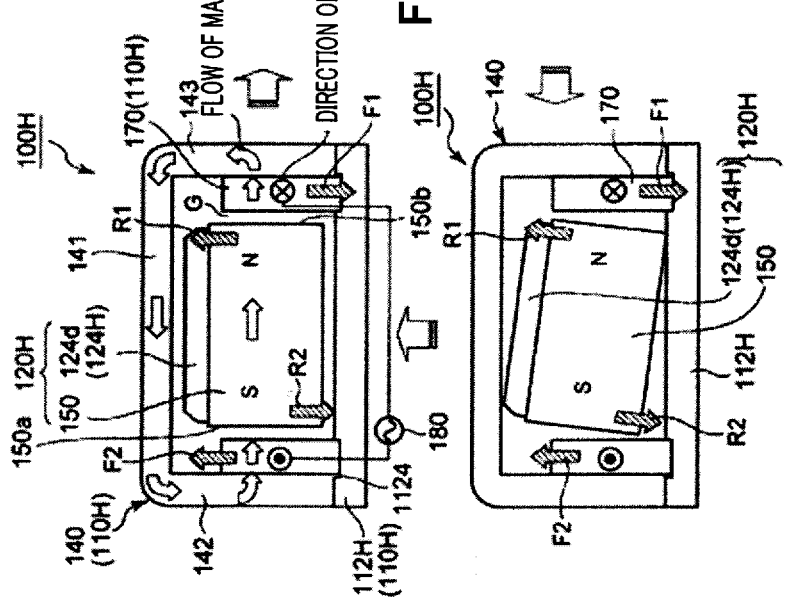
FIG.24A FIG.24B FIG.24C FIG.24D

ACTUATOR AND ELECTRIC TOOTHBRUSH USING ACTUATOR

TECHNICAL FIELD

The present invention relates to an actuator used in, for example, an electric toothbrush or an electric sonic wave toothbrush.

BACKGROUND ART

Electric toothbrushes including electric sonic wave toothbrushes known heretofore include a bass brushing tooth brush places the brush in the part between the tooth and the gum at an angle (at an angle of approximately 45 degrees) and vibrates the brush to the right and left in back-and-forth linear motion, a rolling brushing toothbrush that rotates back and forth (forward and backward) over a predetermined angle range around a shaft and moves from the gum to the tooth rotating, and so on.

The drive of toothbrushes like these involves many structures for converting the rotation of a rotating DC motor that rotates regularly around a shaft into back-and-forth linear motion or back-and-forth rotating motion, via a motion direction converting mechanism. Furthermore, besides these structures, a structure to move a toothbrush in back-and-forth linear motion by means of a linear drive actuator, and a structure to move a toothbrush in back-and-forth rotating motion by making a resonance vibrating mechanism apart from the drive source resonate by the vibration of an actuator, are known.

With an electric toothbrush structured to move the brush part in back-and-forth linear motion by means of a linear drive actuator, as shown in patent literature 1, the linear actuator directly produces back-and-forth vibration in the axial direction of an output shaft that is directly connected with the brush part, and makes possible bass brushing. With this structure, there is little power loss due to a motion converting mechanism, and makes possible fast vibration.

Furthermore, with an electric toothbrush of a structure having an actuator and resonance vibrating mechanism apart from the drive source, as shown in patent literature 2, a drive means with an electro magnet and permanent magnet vibrates the resonance vibrating mechanism having a lever arm. By this means, the lever arm that is coaxially connected with the brush part moves in swinging motion, making possible rolling brushing.

CITATION LIST

Patent Literature

PTL 1
Japanese Patent Application Laid-Open No. 2002-078310
PTL 2
Japanese Patent Publication No. 3243529

SUMMARY OF INVENTION

Technical Problem

Now, to make possible rolling brushing with an electric toothbrush and to make the handle part in which the drive part to drive a rolling brushing toothbrush is accommodated as thin as possible, there is a demand to miniaturize the toothbrush drive part.

However, to realize rolling brushing using a regular motor that rotates around a shaft, apart from this motor, a motion direction converting mechanism to covert the rotation of this motor into back-and-forth rotating motion is necessary. Also, to realize rolling brushing using a linear drive actuator as shown in patent literature 1, apart from this linear drive actuator, a torque generating mechanism (drive source) is necessary.

Also, the structure shown in patent literature 2 requires a drive source as well as a resonance vibrating mechanism apart from the drive source.

Consequently, with conventional structures, if a motor or a linear drive actuator is used as a drive source of an electric toothbrush, it is necessary to secure a space for placing a drive source, and, in addition, a motion direction converting mechanism, a torque generating mechanism, or a resonance vibrating mechanism, apart from the drive source, and there is therefore problem that it is difficult to miniaturize the toothbrush.

In addition, in the event a drive transmitting mechanism (e.g. motion direction converting mechanism) is provided apart from an actuator (e.g. motor) as a toothbrush drive part, there is a threat of producing noise in the drive transmitting mechanism and there is furthermore a threat that the drive transmitting mechanism suffers poor efficiency due to power loss, and it is necessary to take measures against these.

In view of the above, it is an object of the present invention to provide a small actuator and electric toothbrush that can realize back-and-forth rotating motion of an electric toothbrush or the like without using a drive transmitting mechanism apart from a drive source.

Solution to Problem

An actuator according to the present invention adopts a configuration having: a permanent magnet; an outer yoke that has inner wall parts that oppose magnetic pole planes of different poles in the permanent magnet a predetermined interval apart; a coil that is placed between the magnetic pole planes of different poles and the inner wall parts of opposing the magnetic pole planes of different poles and surrounds the permanent magnet; a movable body that has one of the permanent magnet and the coil; a fixed body that has the other one of the permanent magnet and the coil, and the outer yoke, and supports the movable body in a movable fashion via an elastic support part; and an alternating current supplying part that supplies an alternating current of substantially a same frequency as a resonance frequency of the movable body, to the coil.

An actuator according to the present embodiment adopts a configuration having: a fixed body having a permanent magnet and an outer yoke which has inner wall planes opposing magnetic pole planes of different poles of the permanent magnet a certain interval apart; a movable body having a coil that is placed between the magnetic pole planes of different poles and the inner wall planes opposing the magnetic pole planes of different poles and that surrounds the permanent magnet, the movable body being supported in a movable fashion via an elastic support member attached to the fixed body; and an alternating current supplying part that supplies an alternating current of substantially the same frequency as a resonance frequency of the movable body, to the coil.

An actuator according to the present invention has: a movable body that has a permanent magnet, an outer yoke that covers a coil that surrounds the permanent magnet and that has an inner periphery part that opposes the magnetic pole planes of the permanent magnet a certain interval apart, and an outer periphery part of the coil; a fixed body that supports the movable body in a movable fashion via an elastic support part; and an alternating current supplying part that supplies an alternating current of substantially the same frequency as a resonance frequency of the movable body, to the coil.

An electric toothbrush according to the present invention adopts a configuration having: an actuator of the above configuration; and a toothbrush part that is coaxially coupled with the output shaft, at a head of the toothbrush part a hair bundle part being provided to be perpendicular to an axial direction.

Advantageous Effects of Invention

According to the present invention, it is possible to achieve back-and-forth rotating motion of an electric toothbrush or the like without using a drive transmitting mechanism apart from a drive source, so that it is possible to miniaturize an actuator and electric toothbrush.

BRIEF DESCRIPTION OF DRAWINGS

FIG. 10 is a schematic view for explaining operation of this actuator;

FIG. 19 is a schematic view for explaining operation of an actuator according to the seventh embodiment of the present invention;

FIG. 24 is a schematic view for explaining operation of an actuator according to the ninth embodiment of the present invention;

DESCRIPTION OF EMBODIMENTS

Now, embodiments of the present invention will be described below in detail with reference to the accompanying drawings.

(First Embodiment)

Figure 1:
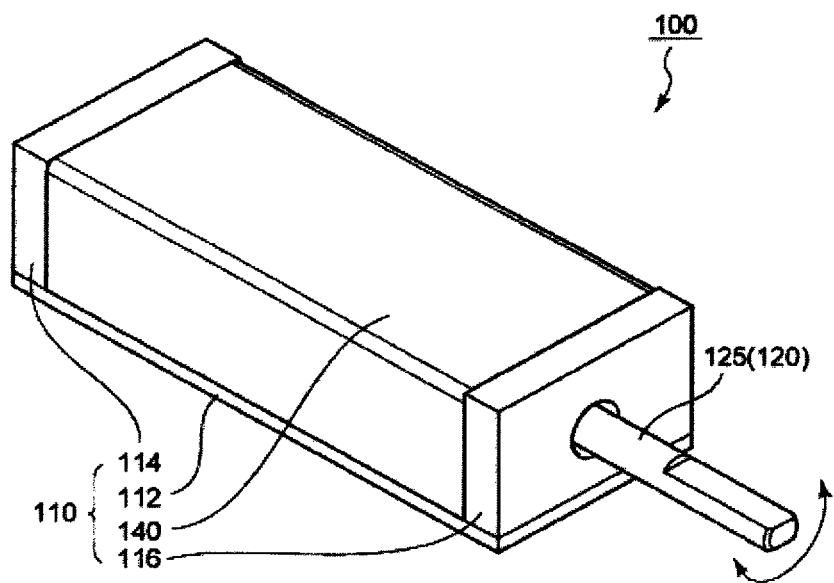
FIG. 1 is a perspective view showing an actuator according to the first embodiment of the present invention.
Figure 2:
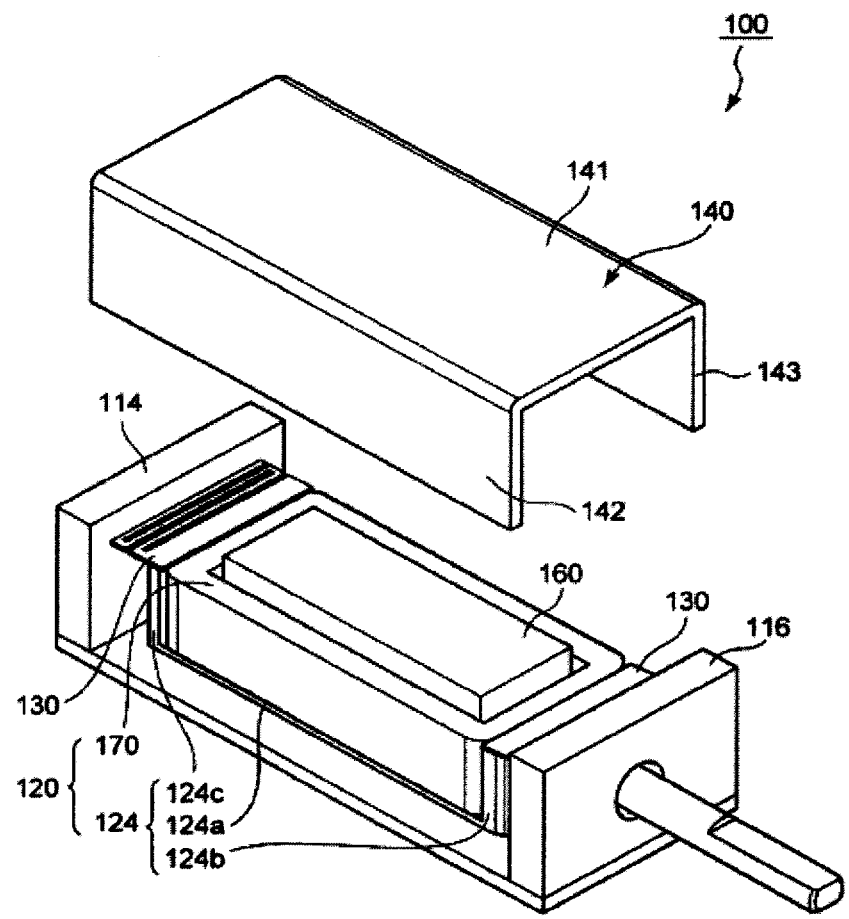
FIG. 2 is a perspective view showing a state an outer yoke is removed from this actuator.

FIG. 1 is a perspective view showing actuator 100 according to the first embodiment of the present invention, and FIG. 2 is a perspective view showing a state an outer yoke is removed from this actuator 100. Also, FIG. 3 is a principal-part exploded perspective view of this actuator.

Figure 3:
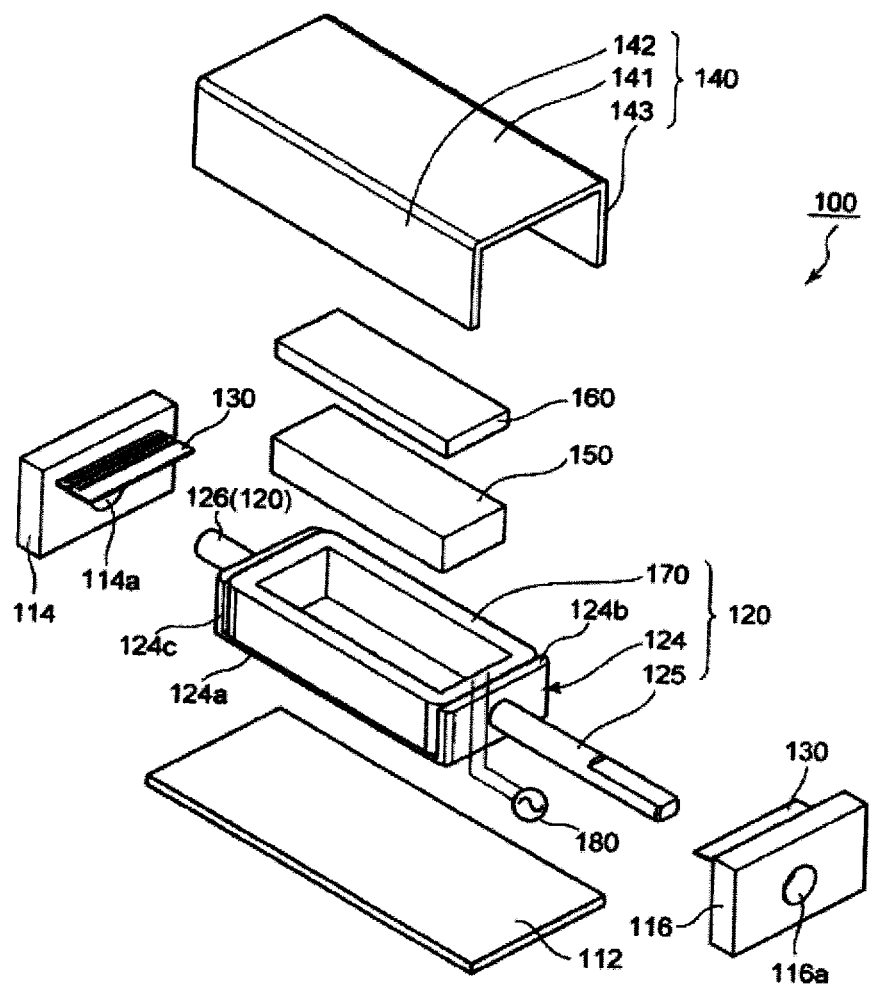
FIG. 3 is a principal-part exploded perspective view of this actuator.

Actuator 100 shown in FIG. 1 through 3 has fixed body 110, movable body 120 (see FIG. 2), elastic members (elastic support parts) 130 (see FIG. 2) that support movable body 120 on fixed body 110 in a movable fashion, and alternating current supplying part 180 (see FIG. 3).

As shown in FIG. 1, with this actuator 100, when movable body 120 (see FIG. 2) that is supported in fixed body 110 via elastic members 130 moves, back-and-forth rotating vibration transmission shaft (hereinafter referred to as "shaft") 125, which is the output shaft of movable body 120, rotates in forward and backward directions (the directions of arrows in FIG. 1) in a predetermined angle range, and outputs back-and-forth rotating vibration outside.

As shown in FIG. 3, fixed body 110 has base plate 112, support wall parts 114 and 116, outer yoke 140, and magnet 150 that is attached to outer yoke 140 via non-magnetic body (spacer) 160.

In fixed body 110, base plate 112 forms a flat rectangular shape that is long in the direction in which shaft 125 extends, and is formed of a non-magnetic body here. Above a center area on the surface of base plate 112, coil 170 of movable body 120 is placed, and outer yoke 140 having a U-shaped cross section (including the shape of a letter U placed sideways) is attached to base plate 112, to cover this coil 170.

Furthermore, support wall parts 114 and 116 are erected from edge parts of base plate 112 that are spaced apart in the long direction.

Support wall parts 114 and 116 have opening parts 114a and 116a in which shafts 125 and 126 of movable body 120 are inserted. Shaft 126 is inserted in opening part 114a, and shaft 125 is inserted in opening part 116a.

Support wall parts 114 and 116 support movable body 120 in a movable fashion via elastic members 130. That is to say, support wall parts 114 and 116 hold movable body 120 in a movable fashion via elastic members 130 in a state in which shafts 125 and 126 are inserted in opening parts 114a and 116a. In a normal state, movable body 120 is supported virtually horizontally (that is, virtually parallel to base plate 112) by means of support wall parts 114 and 116 and elastic members 130. Shafts 125 and 126 may also be loosely inserted in opening parts 114a and 116a. Elastic members 130 will be described later in detail.

Outer yoke 140 is placed between these support wall parts 114 and 116 to cover the main part of movable body 120.

Outer yoke 140 has a cross section approximately in the shape of a letter U that is placed sideways, and is formed by bending a flat magnetic body. Outer yoke 140 has yoke center part 141 of a flat rectangular shape, and mutually opposing sidewall parts 142 and 143 that hang from the side parts of yoke center part 141. In this case, outer yoke 140 is attached to base plate 112 to cover coil 170 and coil holding part 124 of movable body 120, and the tip parts of sidewall parts 142 and 143 are closed by base plate 112.

Outer yoke 140 constitutes a magnetic circuit with coil 170 of movable body 120 to be placed inside and magnet 150 that is attached in yoke center part 141 of outer yoke 140.

Figure 4:
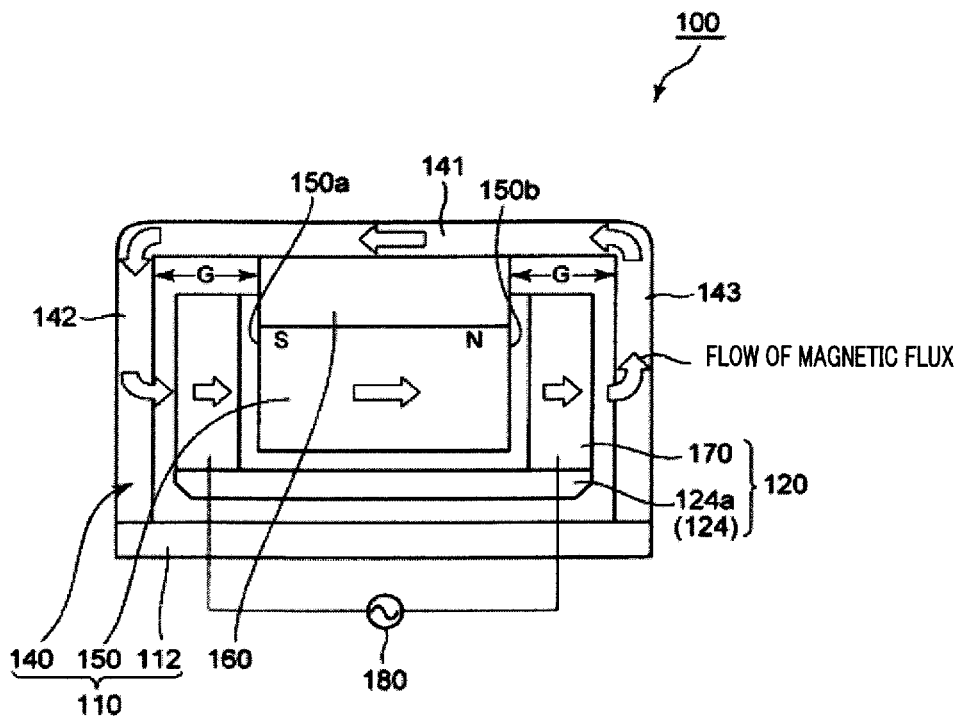
FIG. 4 is a schematic cross-sectional view showing a principal-part configuration of this actuator.

FIG. 4 is a schematic cross-sectional view showing a principal-part configuration of actuator 100.

As shown in FIG. 4, magnet (permanent magnet) 150 is placed in the center area on the back of yoke center part 141 of outer yoke 140, via non-magnetic body 160, such that air gaps G are formed between magnet 150 and opposing sidewall parts 142 and 143 of outer yoke 140.

Magnet 150 is provided to hang from yoke center part 141, via non-magnetic body 160, and different magnetic poles face the inner wall parts of sidewall parts 142 and 143.

That is to say, here, the S-pole end (S magnetic pole plane 150a) of magnet 150 faces the inner wall plane of sidewall part 142 of outer yoke 140, and the N-pole side (N magnetic pole plane 150b) faces the inner wall plane of sidewall part 143 of outer yoke 140.

Furthermore, magnet 150 is a cuboid having a length to match the length of the extension direction of outer yoke 140, and is attached in yoke center part 141, via non-magnetic body 160 having the same outer shape, along the extension direction of yoke center part 141.

By this means, magnet 150 has virtually the same length as the length of the long direction of outer yoke 140, and is placed in yoke center part 141 in a state the inner wall planes of opposing sidewall parts 142 and 143 all face planes of different magnetic poles.

In air gaps G between magnet 150 and sidewall parts 142 and 143 of outer yoke 140, coil 170 of movable body 120 is placed spaced apart from side wall planes (magnetic pole planes) 150a and 150b of magnet 150, inner wall planes of sidewall parts 142 and 143, and the back of yoke center part 141.

Coil 170 is a voice call here and is wound to surround the periphery of magnet 150. To be more specific, in each air gap, coil 170 is wound in a direction perpendicular to the direction in which magnet 150 and sidewall parts 142 and 143 oppose each other. From alternating current supplying part 180, an alternating current supply (AC voltage) is supplied as shown in FIG. 3 and FIG. 4.

This coil 170 is placed in coil holding part 124 and held, and coil holding part 124 is supported by fixed body 110 via elastic members 130.

As shown in FIG. 2 and FIG. 3, this coil holding part 124 is formed in the shape of a letter C placed sideways on a side view, and has bottom plate part 124a on which coil 170 is placed, and front wall part 124b and rear wall part 124c that erect from edge parts of bottom plate part 124a that are spaced apart along the long direction (that is, along the direction in which shaft 125 extends).

This coil holding part 124 is formed of a non-magnetic body. In front wall part 124b, shaft 125 is attached perpendicular, and, in rear wall part 124c, shaft 126 is placed to be positioned coaxially with shaft 125. That is to say, shaft 125 is placed approximately along the center of magnet 150, approximately parallel to varying magnetic pole planes 150a and 150b of magnet 150 (see FIG. 4).

Thus, with coil holding part 124 and shafts 125 and 126, coil 170 constitutes movable body 120 that is supported in a movable fashion, by means of support wall parts 114 and 116.

Elastic members 130 support movable body 120 in the area between opposing support wall parts 114 and 116 such that movable body 120 is able to move in the front, back, left and right directions, and also supports movable body 120 in twisting directions of magnet 150 and shaft 125.

Here, elastic members 130 are formed with flat, zigzag springs that project virtually horizontally in opposing directions in upper end areas of the opposing planes of support wall parts 114 and 116. That is to say, elastic members 130 are each formed with a thin, band-shaped metallic plate of a zigzag shape that repeats, from its one end to the other end, extending in one width direction and returning in the other width direction, and elastic members 130 are each able to compress in a twisting direction if one end and the other end are fixed.

Via elastic members 130 configured in this way, in the area surrounded by base plate 112 and outer yoke 140, movable body 120 is supported by both support wall parts 114 and 116 of fixed body 110 to be able to move in twisting directions about the axis of shafts 125 and 126.

Incidentally, as shown in FIG. 1 and FIG. 2, shaft 125 of movable body 120 is provided to project outward from support wall part 116 in the same direction as the direction of extension of outer yoke 140. That is to say, in actuator 100, shaft 125 is provided to project in a direction that is virtually perpendicular to the direction magnet 150 and sidewall parts 142 and 143 oppose each other.

Shaft 125 is fixed in front wall part 124b of coil holding part 124 in this way, and, by this means, is attached to movable body 120 to be located on an axis to pass the center of gravity of movable body 120. By this means shaft 125 is able to move in back-and-forth rotating vibration with coil 170 and coil holding part 124 constituting the main body of movable body 120, and transmit this vibration outside.

When actuator 100 is used for an electric toothbrush, a toothbrush part is coaxially coupled with shaft 125, and, at the head of this toothbrush part, a hair bundle part is provided to be perpendicular to the axial direction. By this means the toothbrush part moves in the same motion as shaft 125, that is, moves in rolling motion, which is back-and-forth rotating vibration.

With actuator 100 of the present embodiment, assuming that the inertia of movable body 120 is J and the spring constant in a twisting direction is $k_{sp}$, as compared with fixed body 110, movable body 120 vibrates in a resonance frequency calculated based on equation 1 below:

(Equation 1)

$$f_0 = \frac{1}{2\pi}\sqrt{\frac{K_{sp}}{J}} \quad [1]$$

In actuator 100 of the present embodiment, an alternating current of substantially the same frequency as a resonance frequency $f_0$ of movable body 120 is supplied from alternating current supplying part 180 to coil 170. By this means, it is possible to drive movable body 120 efficiently.

As shown in FIG. 4, in fixed body 110 and movable body 120, outer yoke 140, magnet 150 and coil 170 form a magnetic circuit.

Actuator 100 has a magnetic circuit where magnetic fluxes produced from magnet 150 (designated by outline arrows) pass an air gap where coil 170 is placed, sidewall part 143 of outer yoke 140, yoke center part 141, sidewall part 142 and the opposite air gap, in order, and reaches the opposite pole of magnet 150.

Movable body 120 of this actuator 100 is supported by a spring mass system structure supported by fixed body 110 via elastic members 130. When an alternating current of the same frequency as resonance frequency $f_0$ of movable body 120 is supplied to coil 170, movable body 120 is driven in a resonant state. The back-and-forth rotating vibration that is produced then is transmitted to shaft 125 of movable body 120.

Actuator 100 is driven based on the equation of motion represented by equation 2 below and based on the circuit equation represented by equation 3 below.

(Equation 2)

$$J\frac{d^2\theta(t)}{dt^2} = K_t i(t) - K_{sp}\theta(t) - D\frac{d\theta(t)}{dt} - T_{Load} \quad [2]$$

J: Inertia moment [Kgm2]
θ(t): Angle [rad]
$K_t$: Torque constant [Nm/A]
i(t): Current [A]
$K_{sp}$: Spring constant [Nm/rad]
D: Attenuation coefficient [Nm/(rad/s)]
$T_{LOAD}$: Load torque [Nm]

(Equation 3)

$$e(t) = Ri(t) + L\frac{di(t)}{dt} + K_e\frac{d\theta(t)}{dt} \quad [3]$$

e(t): Voltage [V]
R: Resistance [Ω]
L: Inductance [H]
$K_e$: Counter electromotive force multiplier [V/(rad/s)]

That is to say, the inertia moment, rotation angle, torque constant, current, spring constant, attenuation coefficient, and load torque in actuator 100 can be changed as adequate in a range to satisfy equation 2, and the voltage, resistance, inductance, and counter electromotive force multiplier can be changed as adequate in a range to satisfy equation 3.

Next, the operations of actuator 100 will be described in detail.

Figures 5A, 5B, 5C, 5D:
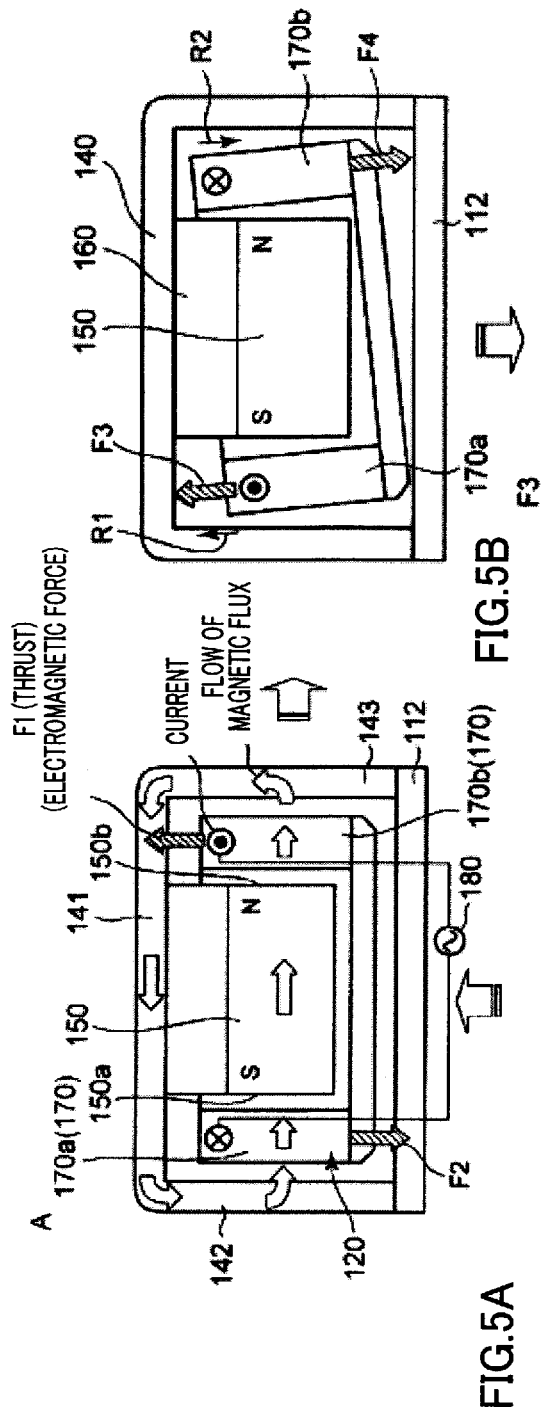
FIG. 5 is a schematic view for explaining operation of this actuator.

FIG. 5 is a schematic view for explaining operation of actuator 100 according top the first embodiment. Although the flow of magnetic fluxes from magnet 150 is shown by outline arrows in FIG. 5A, the same flow applies to FIG. 5B to FIG. 5D, and illustration is omitted in FIG. 5B to FIG. 5D. Also, although FIG. 5A shows alternating current supplying part 180 that supplies an AC voltage to coil 170, the same applies to FIG. 5B to FIG. 5D, and illustration is omitted in FIG. 5B to FIG. 5D.

When an alternating current is supplied from alternating current supplying part 180 to coil 170, thrusts F1, F2, F3 and F4 are produced in coil 170, following Fleming's left hand rule. By this means, in movable body 120 that is attached to base plate 112 and support wall parts 114 and 116 via elastic members 130 in a movable fashion, a rotating force about an axial center at the center of rotation is produced.

One operation cycle of actuator 100 will be described.

When a current flows in coil 170 in the direction shown in FIG. 5A (a current to flow in this direction will be hereinafter referred to as "forward current"), upward thrust F1 (directed toward outer yoke 140) is produced in part 170b of coil 170 opposing N-pole plane 150b of magnet 150. Meanwhile, in part 170a of coil 170 opposing S pole plane 150a of magnet 150, downward thrust F2 (directed toward base plate 112) is produced.

By this means, a rotating force is produced in movable body 120 that has coil 170 and that is supported by support wall parts 114 and 116 that erect from base plate 112 of fixed body 110 (see FIG. 2 and FIG. 3), via elastic members 130. Movable body 120 moves anticlockwise to assume the position shown in FIG. 4B by thrusts F1 and F2 of coil 170.

In the state shown in FIG. 5B, actuator 100 produces reaction forces, designated by arrows R1 and R2, by the restoring force of elastic members 130 (see FIG. 2 and FIG. 3). From the state shown in FIG. 5B to the state shown in FIG. 5D, a reverse current is supplied to coil 170 as compared with FIG. 5A. By this means, from the state shown in FIG. 5B to the state shown in FIG. 5C, movable body 120 rotates anticlockwise with respect to fixed body 110 by the reaction forces designated by arrows R1 and R2 and by the thrusts designated by arrows F3 and F4. From the state shown in FIG. 5C to the state shown in FIG. 5D, movable body 120 rotates anticlockwise with respect to fixed body 110 by the thrusts designated by arrows F3 and F4.

In the state shown in FIG. 5D, actuator 100 produces reaction forces, designated by arrows R3 and R4, by the restoring force of elastic members 130. From the state shown in FIG. 5D to the state shown in FIG. 5A, a forward current is supplied to coil 170. By this means, from the state shown in FIG. 5D to the state shown in FIG. 5A, movable body 120 rotates anticlockwise with respect to fixed body 110 by the reaction forces designated by arrows R3 and R4 and by the thrusts designated by arrows F1 and F2.

From the state shown in FIG. 5A to the state shown in FIG. 5B, movable body 120 rotates anticlockwise with respect to fixed body 110 by the thrusts designated by arrows F1 and F2. Although movable body 120 operates in back-and-forth rotating vibration about magnet 150, but movable body 120 is also able to operate in the same way as shown in FIG. 5 by thrusts F1 to F4, without using the reaction force of elastic members 130.

Next, what alternating current is supplied to coil 170 of movable body 120 in each state shown in FIG. 5 will be described briefly.

FIG. 6 shows the cycle of alternating current supplied from alternating current supplying part 180 to coil 170 of movable body 120 in the actuator according to the present invention.

Figures 6A, 6B:
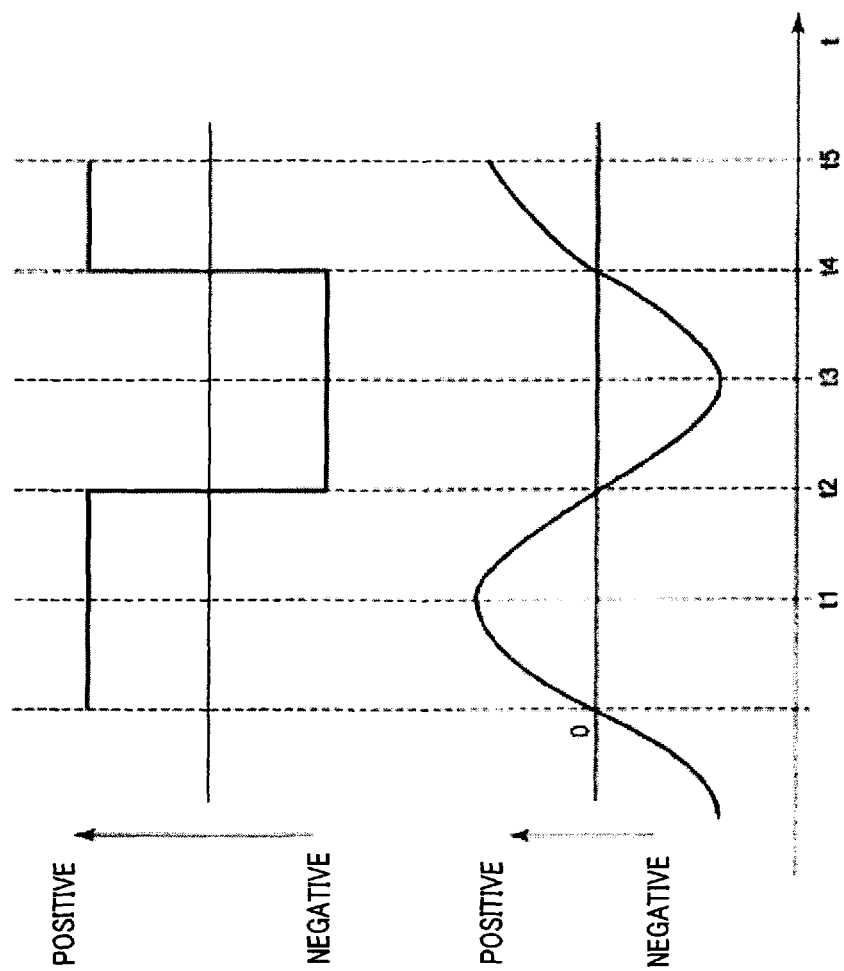
FIG. 6 shows a cycle of alternating current supplied from an alternating current supplying part to a coil.

The alternating current to flow in the coil may be a pulse wave of frequency $f_0$ as shown in FIG. 6A or may be a sine wave of frequency $f_0$ as shown in FIG. 6B.

In the state of FIG. 5A, the forward current at time point t1 shown in FIG. 6 is supplied. In the state of FIG. 5B, the direction of the current is switched as shown at time point t2 in FIG. 6. In the state of FIG. 5C, the reverse current at time point t3 shown in FIG. 6 is supplied. Also, in the state of FIG. 5D, the direction of the current is switched as shown at time point t4 in FIG. 6, and, in the state of FIG. 5D, the forward current at time point t5 shown in FIG. 6 is supplied. This is one operation cycle, and, by repeating these operations, movable body 120 repeats the displacement operations shown in FIG. 5A to FIG. 5D, and, by this means, produces back-and-forth rotating vibration.

In actuator 100, movable body 120 produces back-and-forth rotating motion (that is, back-and-forth rotating vibration), and this back-and-forth rotating vibration is sent outside via shaft 125. When a toothbrush part is coupled with shaft 125 and a hair bundle part is provided to be perpendicular to the axial direction at the head of this toothbrush part, the toothbrush part moves in back-and-forth rotating vibration and makes possible rolling brushing.

By this means, actuator 100 satisfies equations 2 and 3 and is driven by a resonance phenomenon using the resonance frequency represented by equation 1. By this means, in actuator 100, the power to be consumed in a static state is only the loss due to load torque and the loss due to friction and the like, so that low power drive is possible—that is, it is possible to move movable body 120 in back-and-forth rotating vibration at low power consumption. As described above, with actuator 100 of the present embodiment, it is possible to realize back-and-forth rotating motion of an electric toothbrush or the like without using a drive transmitting mechanism apart from a drive source, and furthermore make possible back-and-forth rotating motion at low power consumption.

Furthermore, with this actuator 100, movable body 120 is driven using coil 170 which is a voice coil, so that a detent force, which is magnetic attraction, is not produced, and therefore excellent controllability is provided. To be more specific, the position of movable body 120 while stopped is secured at the center location by the restoring force of elastic members 130, so that there is little power loss when the drive stops.

Furthermore, movable body 120 is formed with coil 170 and coil holding part 124, not including outer yoke 140. Consequently, the scale of the inertia moment of movable body 120 does not depend on the outer shape and is determined based upon the shape of coil 170. Coil 170 is placed inside outer yoke 140 and is unlikely to be a factor to increase the inertia. The increase of inertia moment due to change of the outer shape of actuator 100 is reduced, so that constraints are removed in terms of design, and it is therefore possible to improve the freedom of design with respect to actuator 100 itself.

An electric toothbrush having actuator 100 provides the same advantage, so that it is possible to miniaturize the electric toothbrush itself.

(Second Embodiment)

In the configuration of actuator 100 according to the first embodiment shown in FIG. 1 through 6, an actuator according to the second embodiment uses a magnetic base, instead of non-magnetic base plate 112. Consequently, the other parts are the same as in actuator 100, and their detailed descriptions will be omitted.

Figure 7:
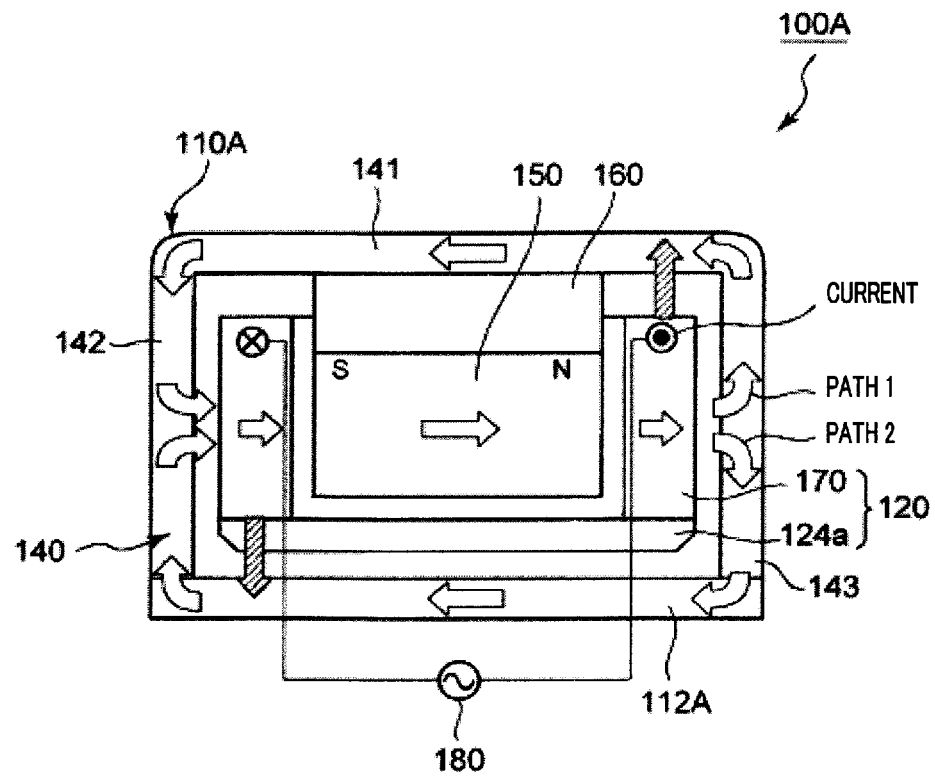
FIG. 7 is a schematic cross-sectional view showing a principal-part configuration of an actuator according to a second embodiment of the present invention.

FIG. 7 is a schematic cross-sectional view showing a principal-part configuration of actuator 100A according to a second embodiment of the present invention. In FIG. 7, the flow of magnetic fluxes in a magnetic circuit by magnet 150 is shown by outline arrows.

Based upon the configuration of actuator 100 according to the first embodiment, actuator 100A is configured such that base plate 112 is made magnetic base plate 112A and movable body 120 having coil 170 is surrounded by a magnetic body. On the inner side of coil 170 surrounded by outer yoke 140 and base plate 112A, similar to the configuration of actuator 100, magnet 150 that is attached to outer yoke 140 a certain gap apart is placed to direct its magnetic pole planes in a direction to cross the direction coil 170 is wound. These magnetic pole planes are placed to sandwich sidewall parts 142 and 143 of outer yoke 140 by coil. With this configuration, compared to actuator 100, actuator 100A forms two paths for magnetic fluxes by magnetic 150 in fixed body 110.

That is to say, as shown in FIG. 7, in the magnetic circuit of actuator 100A, magnetic fluxes (shown by outline arrows) that are produced from magnet 150 reach sidewall part 143 of outer yoke 140 via an air gap where coil 170 is placed. Then, from sidewall part 143 of outer yoke 140, the magnetic fluxes pass both yoke center part 141 and base plate 112A on the opposite side of yoke center part 141, and then arrive at sidewall part 143. Magnetic fluxes passing sidewall part 142 pass the opposite air gap from sidewall part 142 and continue to the opposite pole of magnet 150. The operation of movable body 120 in actuator 100A is virtually the same as in actuator 100, and so descriptions will be omitted here.

By this means, similar to actuator 100, actuator 100A is able to realize back-and-forth rotating motion of a toothbrush and the like without using a drive transmitting mechanism apart from a drive source. In addition, in actuator 100A, the magnetic saturation in the magnetic circuit is reduced, so that it is possible to increase the thrust of movable body 120 that is produced when an AC voltage is supplied from alternating current supplying part 180 to coil 170.

Compared to the configuration of actuator 100 according to the first embodiment, actuator 100A of this second embodiment is able to increase the torque which coil 170 produces to move movable body 120 by 1.05 times.

Furthermore, with this second embodiment, the outer periphery part of fixed body 110 accommodating movable body 120 in a movable fashion—that is, a magnetic circuit including magnet 150—is formed with outer yoke 140, which is a magnetic body, and base plate 112A, which is a magnetic body.

That is to say, by forming the outer surface of actuator 100A using a magnetic body, in actuator 100A, it is possible to prevent magnetic fluxes from leaking from the magnetic circuit including base plate 112A, outer yoke 140, magnet 150 and coil 170.

(Third Embodiment)

Figure 8:
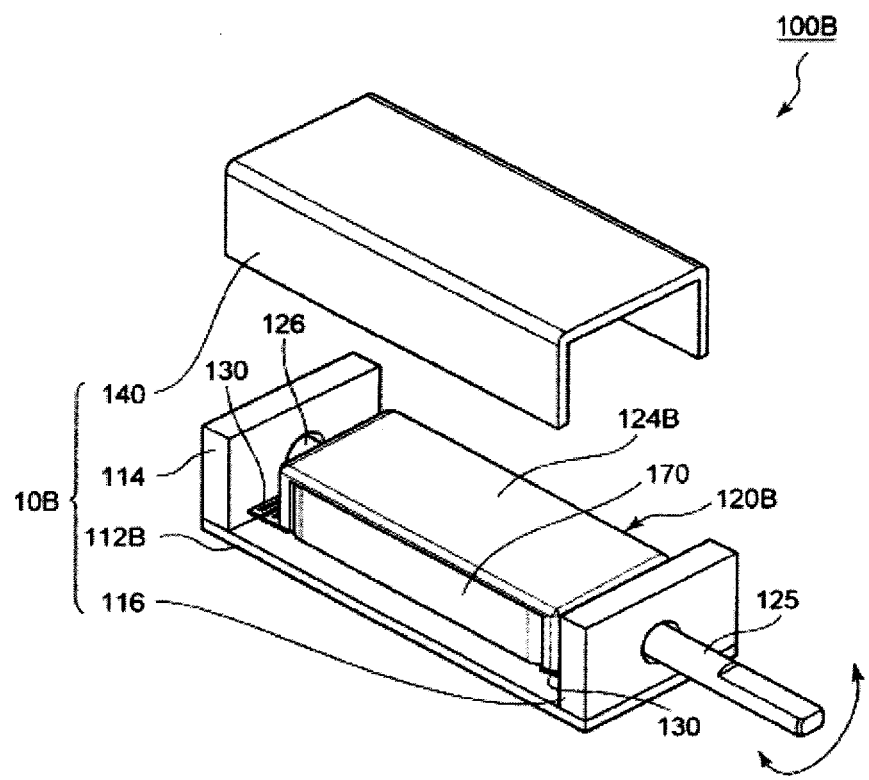
FIG. 8 shows a configuration of an actuator according to a third embodiment of the present invention.
Figure 9:
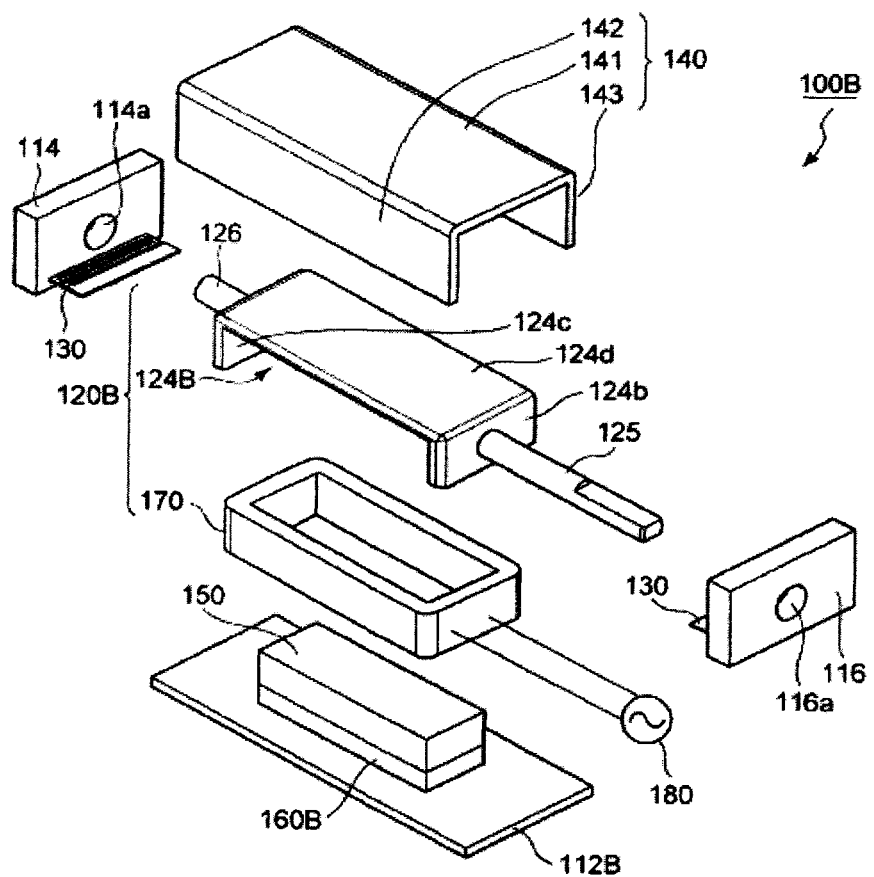
FIG. 9 is an exploded perspective view of this actuator.

FIG. 8 shows a configuration of actuator 100B according to a third embodiment of the present invention and shows a state in which outer yoke 140 is removed from base plate 112B in actuator 100B, and FIG. 9 is an exploded perspective view of this actuator. Actuator 100B basically has the same configuration as actuator 100 according to the first embodiment, shown in FIG. 1, and therefore parts in actuator 100B that are the same as in actuator 100 will be assigned the same reference numerals and codes as in actuator 100 and their explanations will be omitted.

Based upon the configuration of actuator 100 according to the first embodiment, in an actuator according to this third embodiment, magnet 150 is removed from outer yoke 140, fixed on base plate 112 via a non-magnetic body (spacer), and movable body 120 is turned upside down and fixed on fixed body 110 to be able to move in twisting directions in back-and-forth rotating vibration.

To be more specific, actuator 100B has fixed body 110B, movable body 120B, elastic members 130 that support movable body 120B on fixed body 110B so as to be able to move in twisting directions about shaft 125 of movable body 120B, and alternating current supplying part 180 (see FIG. 9 and FIG. 10).

As shown in FIG. 8 and FIG. 9, fixed body 110B has base plate 112B, magnet 150 that is placed on base plate 112B via projection part 160B of a non-magnetic body (spacer), and U-shaped outer yoke 140 that is attached to base plate 112B to cover magnet 150.

In fixed body 110B, flat, rectangular base plate 112B is formed of a non-magnetic body, and magnet 150 is attached, via non-magnetic projection part 160B that is formed to project upward in the center area on the surface.

Magnet 150 is attached on non-magnetic projection part 160B such that air gaps are formed between its differing magnetic pole planes and opposing sidewall parts 142 and 143 of outer yoke 140. Like magnet 150 of the above embodiments, the magnetic pole planes of magnet 150 are spaced apart in a direction perpendicular to shaft 125 and oppose sidewall parts 142 and 143 of outer yoke 140.

Projection part 160B is formed on base plate 112B integrally and has the same outer shape as magnet 150. Here, projection part 160B is a cuboid to extend, with magnet 150, in the long direction of base plate 112B. Projection part 160B places magnetic 150 apart from base plate 112B, thereby securing an area to allow coil 170 of movable body 120B located in the surroundings of magnet 150 to move in back-and-forth rotation about magnet 150.

Thus, movable body 120B is placed on fixed body 110B such that coil 170 and upper plane part 124d of coil holding part 124B are placed over magnet 150 attached on projection part 160B projecting from base plate 112B.

Movable body 120B is placed in an air gap formed between opposing inner wall part planes of outer yoke 140 and magnet 150, and is formed with coil 170 that surrounds magnet 150, and coil holding part 124B that holds coil 170.

In coil holding part 124B where front wall part 124b and rear wall part 124c hang from edge parts of upper plane part 124d that are spaced part in the log direction, coil 170 is attached on the back of upper plane part 124d.

Coil holding part 124B is attached to support wall parts 114 and 116 of fixed body 110B, via elastic members 130, to be able to move in twisting directions about shafts 125 and 126 provided perpendicular to the axial direction of coil 170. Elastic members 130 are formed on support wall parts 114 and 116 integrally by means of insert molding.

Similar to actuator 100 of the first embodiment and actuator 100A of the second embodiment, an alternating current having approximately the same frequency as a resonance frequency is supplied to coil 170 from alternating current supplying part 180 that supplies an AC voltage. By this means, movable body 120B, supported in fixed body 110B by means of elastic members 130 to be able to move in twisting directions of shaft 125, moves in back-and-forth rotating vibration by the thrust by coil 170 in fixed body 110B.

FIG. 10 is a schematic diagram for explaining the operation of actuator 100B according to the third embodiment of the present invention. Although the flow of magnetic fluxes from magnet 150 is shown by outline arrows in FIG. 10A, the same flow applies to FIG. 10B to FIG. 10D, and illustration is omitted in FIG. 10B to FIG. 10D. Also, although FIG. 10A shows alternating current supplying part 180 that supplies an AC voltage to coil 170, the same applies to FIG. 10B to FIG. 10-D, and illustration is omitted in FIG. 10B to FIG. 10D.

As shown in FIG. 10A, actuator 100B has a magnetic circuit where magnetic fluxes produced from magnet 150 (designated by outline arrows) pass air gap G where coil 170 is placed, sidewall part 143 of outer yoke 140, yoke center part 141, sidewall part 142 and the opposite air gap, in order, and reaches the opposite pole of magnet 150.

With actuator 100B, when an alternating current is supplied from alternating current supplying part 180 to coil 170, thrusts F1, F2, F3 and F4 are produced in coil 170, following Fleming's left hand rule. By this means, a rotating force about an axial center being shaft 125, which is the center of rotation, is produced in coil 170, and, similar to the case of coil 170 of actuator 100 shown in FIG. 5, movable body 120 repeats the operations of FIG. 10A, FIG. 10B, FIG. 10C, and FIG. 10D, and produces back-and-forth rotating vibration.

In this way, with actuator 100B, magnet 150 is directly placed on projection part 160B that is formed on non-magnetic base plate 112B integrally, so that, compared to actuator 100 of the first embodiment, it is not necessary to use a separate non-magnetic body and it is therefore possible to reduce the number of parts and make actuator 100B cost effective.

Furthermore, upon assembly, magnet 150 is placed on projection part 160B that projects from the surface of flat base plate 112B, so that, compared to the case of placing magnet 150 in the denting interior of U-shaped outer yoke 140, it is possible to perform positioning and assembling operations easily. Furthermore, although actuator 100B places magnet 150 differently compared to actuator 100, the magnetic circuit configuration is the same and the same effect as actuator 100 of the first embodiment can be provided. In particular, with actuator 100B, it is possible to achieve back-and-forth rotating motion of an electric toothbrush or the like without using a drive transmitting mechanism apart from a drive source.

(Fourth Embodiment)

Figure 11:
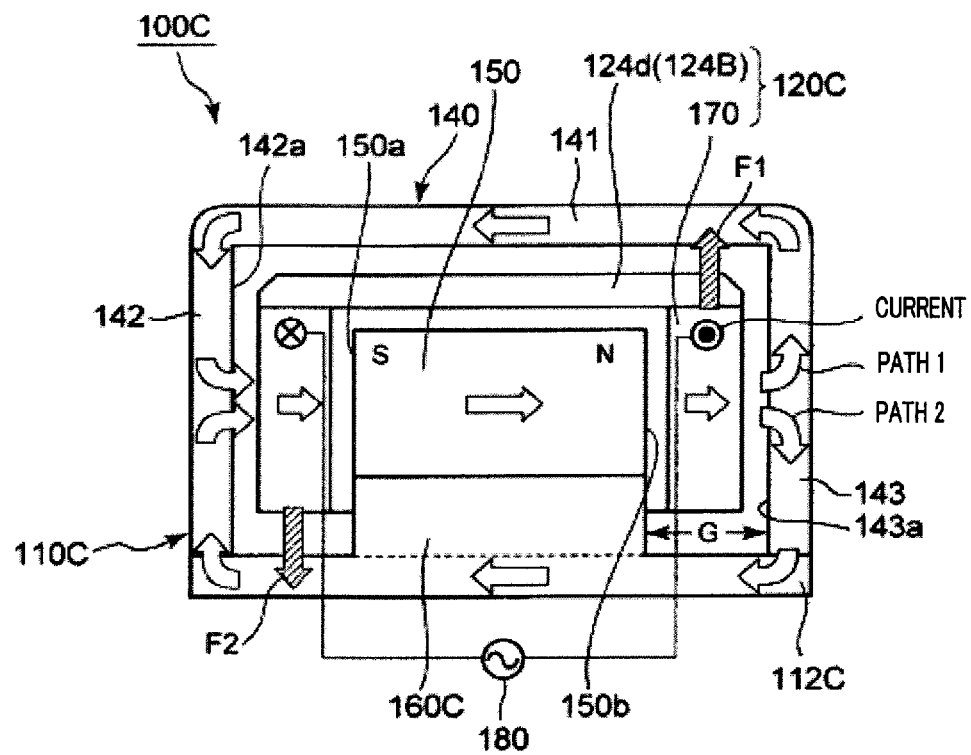
FIG. 11 is a schematic cross-sectional view showing a principal-part configuration of an actuator according to a fourth embodiment of the present invention.

FIG. 11 is a schematic cross-sectional view showing a principal-part configuration of actuator 100C according to a fourth embodiment of the present invention, and also is a schematic cross sectional view showing configurations of a fixed body and movable body in actuator 100C. In FIG. 11, the flow of magnetic fluxes in actuator 200C is shown by outline arrows.

Based upon the configuration of actuator 100B shown in FIG. 8 and FIG. 9, actuator 100C according to this fourth embodiment has a configuration to replace non-magnetic base plate 112B with magnetic base plate 112C, and the other configurations are the same.

That is to say, with actuator 100C, magnet 150, having differing magnetic poles that are horizontally apart, is placed in approximately the center area on the surface of magnetic base plate 112C of a flat rectangular shape. U-shaped outer yoke 140 is placed on base plate 112C to cover magnet 150. Inner wall parts 142a and 143a of sidewall parts 142 and 143 of outer yoke 140 are placed to oppose different magnetic poles (S magnetic pole plane 150a and N magnetic pole plane 150b) of magnet 150 via air gaps G.

In air gap G, coil 170 is placed to surround magnet 150, and these coils 170 are held by coil holding parts 124B. In this case, similar to the third embodiment, coil holding part 124B inserts shafts 125 and 126 rotatably in opening parts 114a and 116a of support wall parts 114 and 116 (see FIG. 9), and is held via elastic members 130 in a movable fashion. That is to say, movable body 120C is attached to fixed body 110C to be able to move in back-and-forth rotation vibration in twisting directions about shaft 125 (not shown).

In actuator 100C configured this way, magnetic fluxes to flow out from magnet 150 travel on two paths in fixed body 110.

That is to say, in actuator 100C, magnetic fluxes (shown by outline arrows) that are produced from magnet 150 pass an air gap where coil 170 is placed, from N magnetic pole plane 150b, passes base plate 112C from sidewall part 143 from outer yoke 140, passes yoke center part 141 of outer yoke 140 on the opposite side from base plate 112C, and reaches sidewall part 142. The magnetic fluxes then passes an air gap from side wall part 142, and continue to S magnetic pole plane 150a, which is the opposite pole of magnet 150. Similar to actuator 100B, an alternating current having approximately the same frequency as a resonance frequency is supplied to coil 170 from alternating current supplying part 180 that supplies an AC voltage. By this means, movable body 120C, supported in fixed body 110C by means of elastic members 130 to be able to move in twisting directions of shaft 125 (see FIG. 9), moves in back-and-forth rotating vibration by the thrust by coil 170 in fixed body 110C. The back-and-forth rotating vibration of movable body 120c in actuator 100C is the same as actuator 100, and its description will be omitted.

Then, in addition to the working advantages of actuator 100B, the magnetic circuit of actuator 100c can provide the same advantages as by actuator 100A of the second embodiment. In addition, in actuator 100C, magnetic saturation is reduced, so that it is possible to increase the thrust of movable body 120C that is produced when an AC voltage is supplied from alternating current supplying part 180 to coil 170.

Furthermore, the outer periphery part of fixed body 110V accommodating movable body 120C in a movable fashion—that is, a magnetic circuit including magnet 150—is formed with outer yoke 140, which is a magnetic body, and base plate 112C, which is a magnetic body. That is to say, by forming the outer surface of actuator 100C using a magnet body, in actuator 100C, it is possible to prevent magnetic fluxes from leaking from the magnetic circuit including base plate 112C, outer yoke 140, magnet 150 and coil 170.

(Fifth Embodiment)

Figure 12:
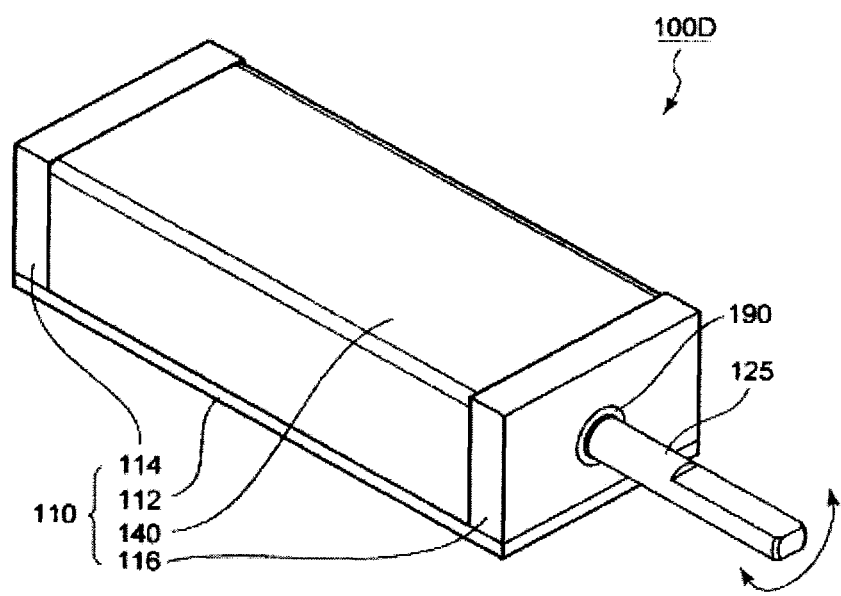
FIG. 12 is a perspective view showing an actuator according to a fifth embodiment of the present invention.
Figure 13:
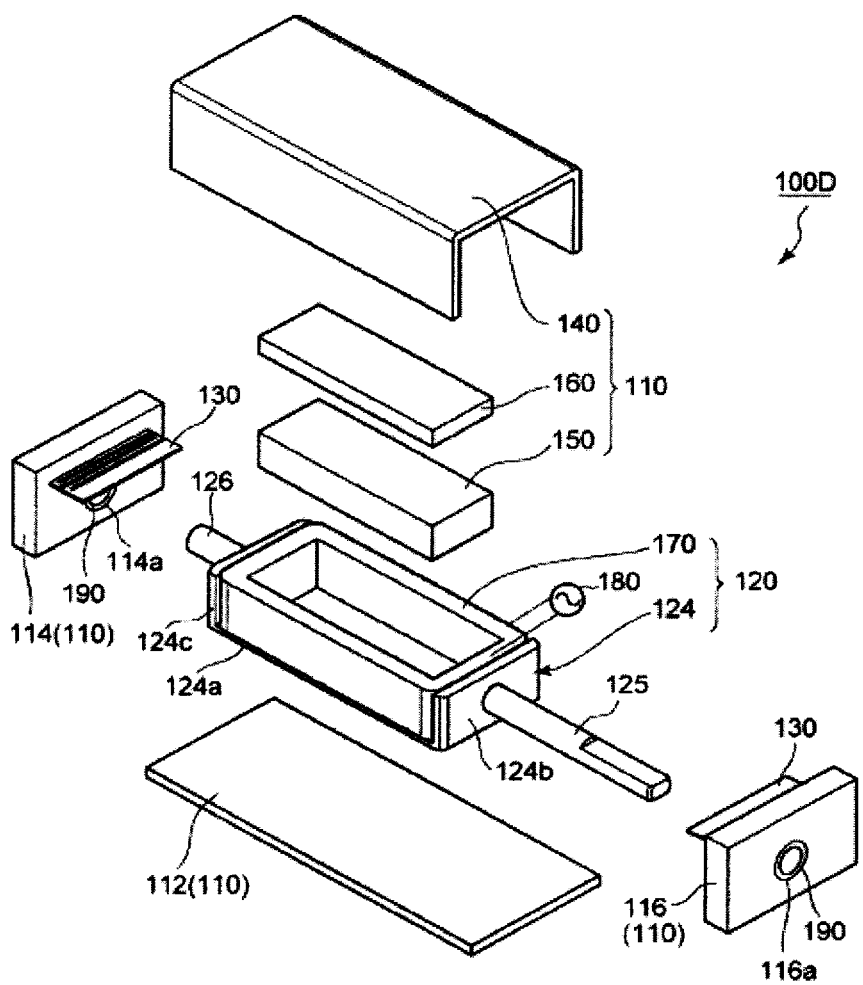
FIG. 13 is a principal-part exploded perspective view of this actuator.

FIG. 12 is a perspective view showing actuator 100D according to a fifth embodiment of the present invention, and FIG. 13 is a principal-part exploded perspective view of this actuator 100D. Actuator 100D basically has the same configuration as actuator 100 according to the first embodiment, shown in FIG. 1, and therefore parts in actuator 100D that are the same as in actuator 100 will be assigned the same reference numerals and codes as in actuator 100 and their explanations will be omitted.

Based upon actuator 100 shown in FIG. 1, actuator 100D according to the fifth embodiment has a configuration in which shafts 125 and 126 are inserted through support wall parts 114 and 116 of fixed body 110 via bearing 190 and axially supported in a rotatable fashion, and the rest of the configurations are the same.

That is to say, as shown in FIG. 12 and FIG. 13, in actuator 100D, shaft 125 which movable body 120 has is rotatably inserted in bearing 190 attached to opening part 116a of support wall part 116. This shaft 125 transmits and outputs the movement/motion of movable body 120, and functions as a bearing to axially support movable body 120 on fixed body 110.

Furthermore, shaft 126 that is placed coaxially with shaft 125 in movable body 120 and that projects in the opposite direction from shaft 125 is rotatably inserted in bearing 190 attached to opening part 114a of support wall part 114.

Consequently, with actuator 100D, when an alternating current is supplied from alternating current supplying part 180 to coil 170, movable body 120 having coil 170 moves in stable back-and-forth rotating vibration about an axial center of shaft 125 with respect to fixed body 110.

In this way, with actuator 100D, movable body 120 is axially supported by support wall parts 114 and 116, via shafts 125 and 126 inserted in bearing 190, in a rotatable fashion, with freedom in the rotating direction and axial direction. Furthermore, in a state in which movement in the axial direction is constrained, movable body 120 is supported by support wall parts 114 and 116 via elastic members 130.

That is to say, movable body 120 uses an axial support structure using support wall parts 114 and 116, shafts 125 and 126 and bearing 190, and is supported in fixed body 110 by securing freedom in the direction of rotation, so that movable body 120 is structured to be strong against shock.

Consequently, actuator 100D is able to achieve the same advantages as by actuator 100, and, in addition, move in stable back-and-forth rotating motion by fixing the axis of rotation of shafts 125 and 126, so that it is possible to improve the robustness of the actuator itself against shock.

Although with this embodiment bearing 190 is provided in support wall parts 114 and 116 in actuator 100 according to the first embodiment to support shafts 125 and 126 of movable body 120 in a rotatable fashion, this is by no means limiting, and other places in actuators 100A, 100B and 100C according to the second to fourth embodiments are equally applicable and available for modification.

(Sixth Embodiment)

Figure 14:
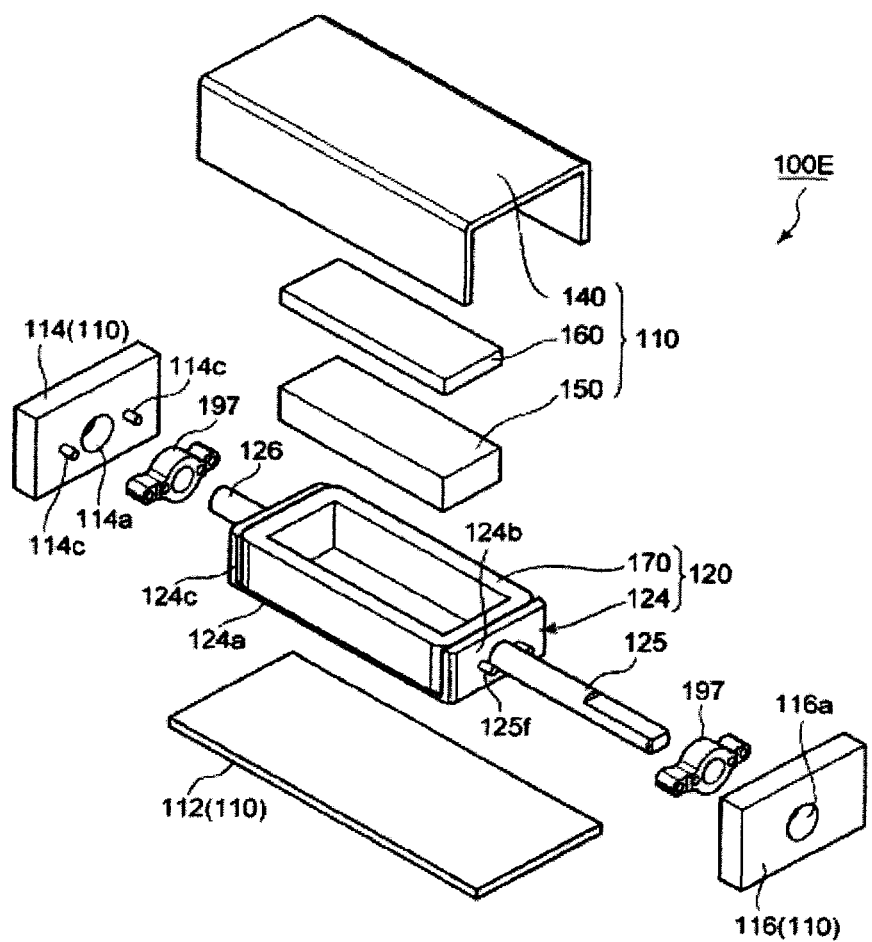
FIG. 14 is a principal-part exploded perspective view of an actuator according to a sixth embodiment of the present invention.
Figure 15:
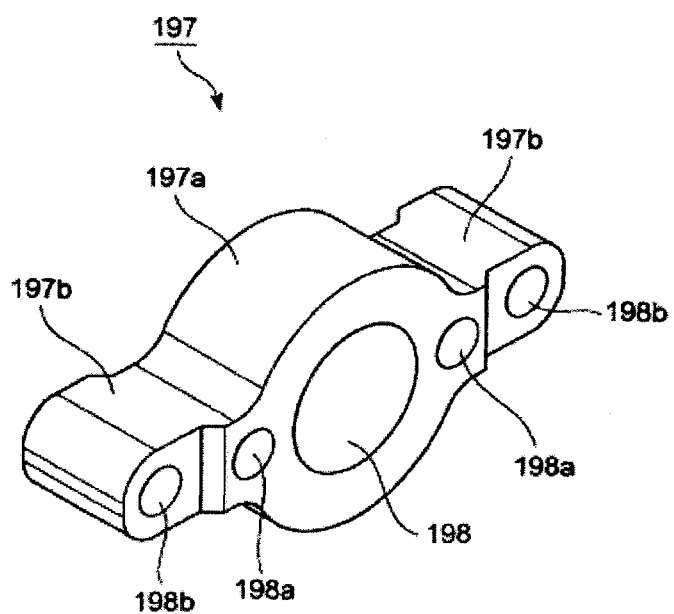
FIG. 15 shows an elastomer, which is a viscoelastic member used in this actuator.

FIG. 14 is a principal-part exploded perspective view of an actuator according to a sixth embodiment of the present invention and FIG. 15 shows an elastomer, which is a viscoelastic member used in this actuator. Based upon actuator 100 according to the first embodiments shown in FIG. 14, actuator 100E shown in FIG. 14 replaces the configuration of elastic member 130 and the rest of the configurations are the same. The same parts will be assigned the same reference numerals and codes and their explanations will be omitted.

Based upon the configuration of actuator 100, with actuator 100E, a viscoelastic body which itself attenuates significantly (elastomer 197 here) is used instead of elastic members 130 (which are zigzag springs).

As shown in FIG. 15, elastomer 197 has center part 197a having insertion opening 198 in which shafts 125 and 126 are inserted, and arm parts 197b that project from center part 197a in a direction perpendicular to the axial center of shaft 126 and shaft 125. Elastomer 197 is a viscoelastic body and can be displaced by elastically defining center part 197a and arm parts 197b.

Elastomer 197 is placed between support wall parts 116 and 114 and front wall part 124b and rear wall part124c of coil holding part 124, and function as a spring. In elastomer 197, projections on support walls part 116 and 114 and rear wall parts 124b and 124 are inserted and fit in holes 198a and 198b formed in locations shifted in the direction arm part 197b extends.

FIG. 14 shows only projections 114c formed in support wall part 114 and projections 125f formed in front wall part 124b, out of all projections to be inserted in holes 198a and 198b of elastomer 197. Although not shown, similar projections to projections 114c of support wall part 114 are formed on support wall part 116, and, likewise, similar projections to projections 125f of front wall part 124b are formed in rear wall part 124c. Here, in arm parts 197b of elastomer 197, projections of front and rear wall part124b and 124c are pressed and fit in holes 198a in locations near center part 197a. Furthermore, projections of support wall parts 116 and 114 are pressed and fit in holes 198b in locations father from center part 197a.

Actuator 100E thus has characteristics of the first embodiment and provides the same working advantages as by actuator 100. In addition, by placing elastomer 197 between support wall parts 116 and 114 and front wall part 124b and rear wall part 124c of coil holding part 124, and by pressing projections (only projections 114c and 125f are shown in FIG. 13) in support wall parts 116 and 114, front wall part 124b and rear wall part 124c, into holes 198a and 198b, actuator 100E can be attached to both members. By this means, unlike cases where metallic springs such as zigzag springs and flat springs are used, complex processes of installation such as fastening of screws, bonding and insert molding are not necessary, and it is possible to allow elastomer 197 to function as a spring only by sandwiching elastomer 197 between movable body 120 and fixed body 110, and it is therefore possible to improve the assembly of actuator 100 itself.

Although with actuator 100E movable body 120 is supported on fixed body 110, using elastomer 197 instead of elastic member 130 according the first embodiment, to be able to move in twisting directions about the axis of shafts 125 and 126, this is by no means limiting, and other places in actuators 100A, 100B and 100C are equally applicable and available for modification.

(Seventh Embodiment)

Figure 16:
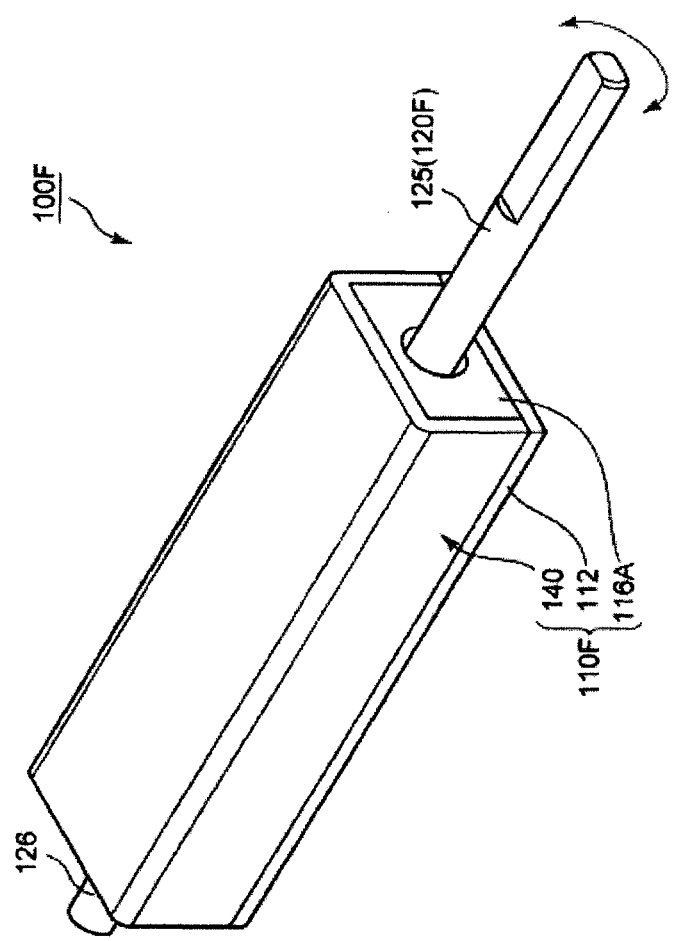
FIG. 16 is a perspective view showing an actuator according to a seventh embodiment of the present invention.
Figure 17:
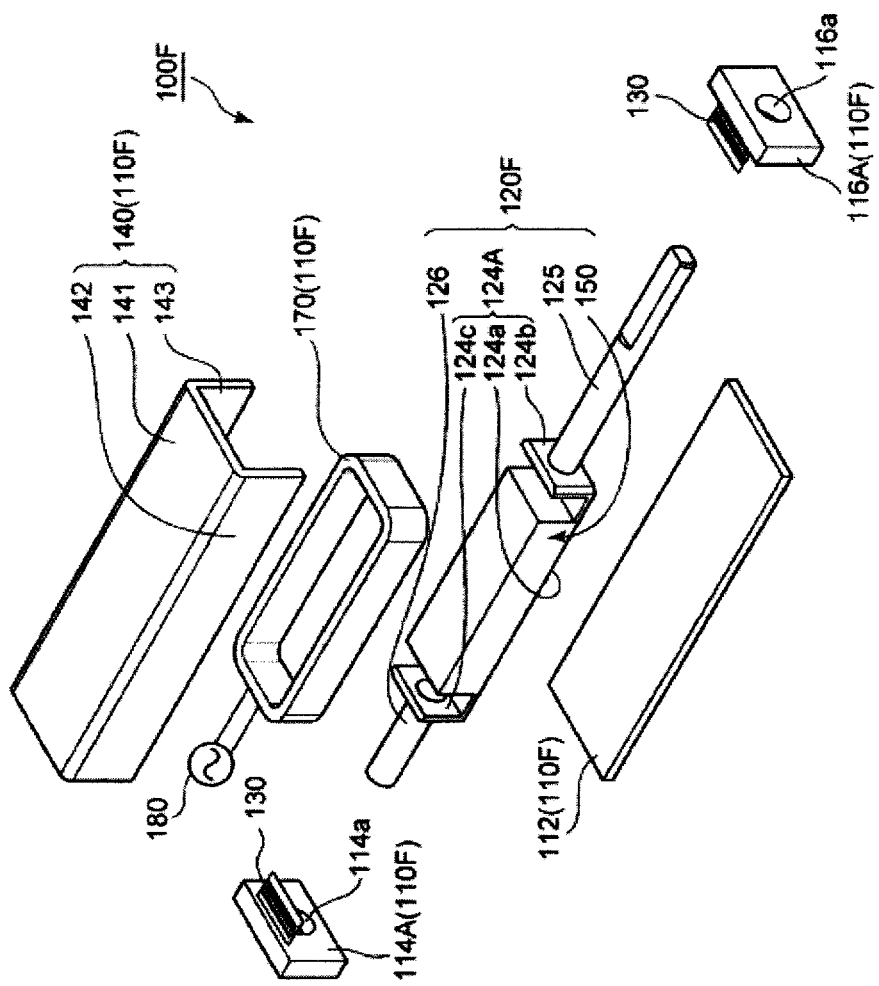
FIG. 17 is a principal-part exploded perspective view of an actuator according to the seventh embodiment of the present invention.

FIG. 16 is a perspective view showing actuator 100F according to a seventh embodiment of the present invention, and FIG. 17 is a principal-part exploded perspective view of this actuator 100F.

Actuator 100F shown in FIG. 16 and FIG. 17 has fixed body 110F, movable body 120F, elastic members (elastic support parts) 130 that support movable body 120F on fixed body 110F in a movable fashion, and alternating current supplying part 180.

With this actuator 100F, when movable body 120F (see FIG. 17) that is supported in fixed body 110F via elastic members 130 moves, back-and-forth rotating vibration transmission shaft (hereinafter referred to as "shaft") 125, which is the output shaft of movable body 120F (see FIG. 17), rotates in forward and backward directions (the directions of arrows in FIG. 16) in a predetermined angle range, and outputs back-and-forth rotating vibration outside.

As shown in FIG. 17, fixed body 110F has base plate 112, support wall parts 114A and 116A, outer yoke 140, and coil 170 that is attached to outer yoke 140. Meanwhile, movable body 120F has magnet (permanent magnet) 150, magnet holding part 124F that is supported by support wall parts 114A and 116A via elastic members 130 and that holds magnet 150, and shafts 125 and 126.

In fixed body 110F, in outer yoke 140, magnet 150 of movable body 120F is placed in an air gap the inner side of coil 170. In actuator 100F, by receiving as input an alternating current supply (AC voltage) from alternating current supplying part 180, movable body 120F is driven in a resonant state.

To be more specific, in fixed body 110F, base plate 112 forms a flat rectangular shape that is long in the direction in which shaft 125 of movable body 120F extends, and is formed of a non-magnetic body here.

Above the surface of base plate 112, magnet 150 of movable body 120F is placed, and outer yoke 140 having a U-shaped cross section (including the shape of a letter U placed sideways) is attached to base plate 112, to cover this coil 170.

Furthermore, support wall parts 114A and 116A are erected from edge parts of base plate 112 that are spaced apart in the long direction.

Support wall parts 114A and 116A have opening parts 114a and 116a in which shafts 125 and 126 of movable body 120F are inserted. In a state in which shafts 126 and 125 are inserted rotatably in opening parts 114a and 116a, respectively, support wall parts 114A and 116A support movable body 120F rotatably via elastic members 130.

In a normal state, with elastic members 130, support wall parts 114A and 116A hold movable body 120F virtually horizontally (virtually parallel to base plate 112). Shafts 125 and 126 in may be inserted in opening parts 114a and 116a loosely.

Elastic members 130 support movable body 120 in the area between opposing support wall parts 114A and 116A such that movable body 120F is able to move in the front, back, left and right directions.

Here, elastic members 130 are formed with flat, zigzag springs that project virtually horizontally in opposing directions in upper end areas of the opposing planes of support wall parts 114A and 116A. That is to say, elastic members 130 are each formed with a thin, band-shaped metallic plate of a zigzag shape that repeats, from its one end to the other end, extending in one width direction and returning in the other width direction, and elastic members 130 are each able to compress in a twisting direction if one end and the other end are fixed.

One end of elastic members 130 configured in this way is attached to support wall parts 114A and 116A by insert molding and the other end is attached to magnet holding part 124F that holds magnet 150. By this means, in the area surrounded by base plate 112 and outer yoke 140, support wall parts 114A and 116A support movable body 120F, via elastic members 130, to be able to move in twisting directions about the axis of shafts 125 and 126.

Figure 18:
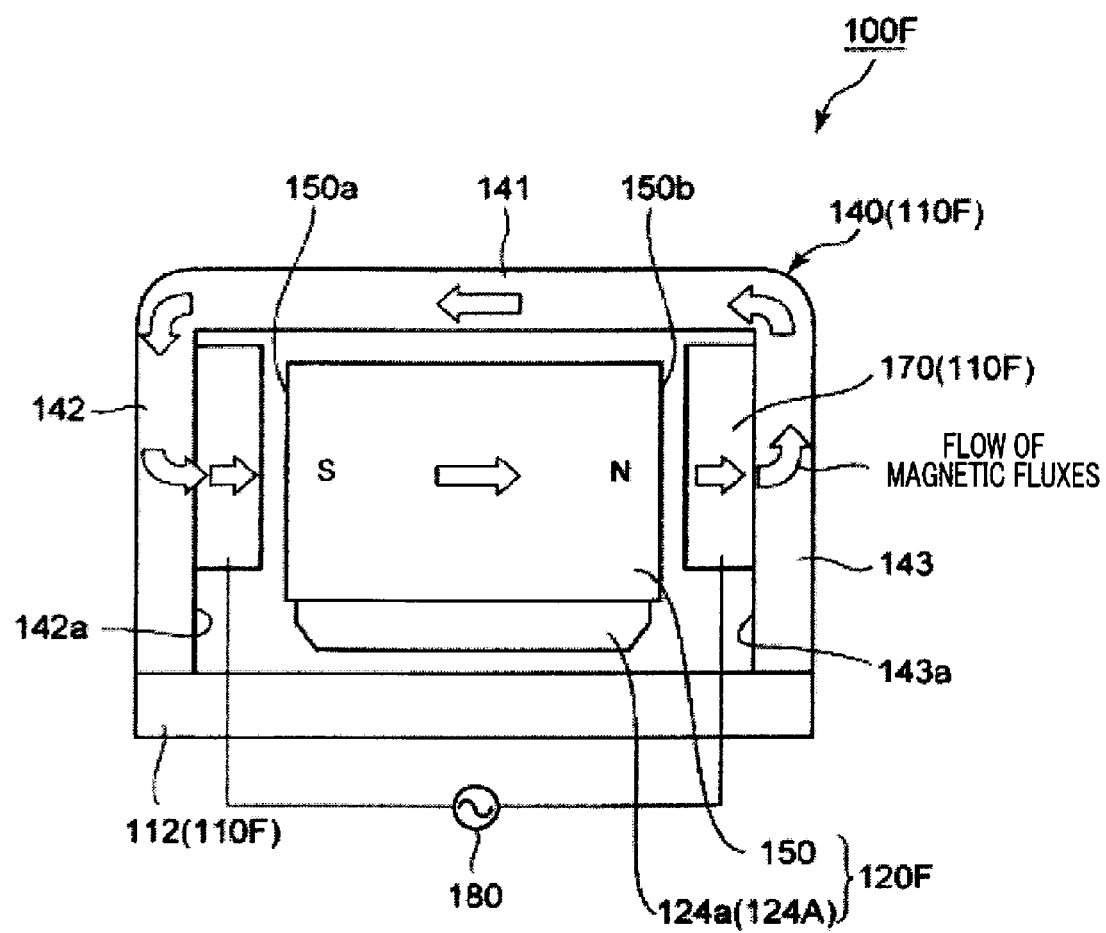
FIG. 18 is a schematic cross-sectional view showing a principal-part configuration of an actuator according to the seventh embodiment of the present invention.

FIG. 18 is a schematic cross-sectional view showing a principal-part configuration of actuator 100F according to the seventh embodiment of the present invention. FIG. 18 shows the flow of magnetic fluxes, from magnet 150 as a magnetic circuit of actuator 100F, with outline arrows.

Outer yoke 140 has an approximately U-shaped cross section, and is formed by bending a flat magnetic body. Outer yoke 140 has yoke center part 141 of a flat rectangular shape, and mutually opposing sidewall parts 142 and 143 that hang from the side parts of yoke center part 141.

Outer yoke 140 here covers base plate 112 and support wall parts 114A and 116A from above, and covers magnet 150 and magnet holding part 124F of movable body 120F. The openings in the tip parts of sidewall parts 142 and 143 are closed by base plate 112, and, with base plate 112 and support wall parts 114A and 116A, outer yoke 112A forms a box shape to accommodate movable body 120F.

In inner wall parts 142a and 143a of opposing sidewall parts 142 and 143 of outer yoke 140, coil 170 that is wound to surround the periphery of magnet 150 of movable body 120F is fixed via air gaps.

Coil 170 is a voice coil here, and is placed such that its outer diameter parts are fixed on inner wall planes 142a and 143a of side wall parts 142 and 143 of outer yoke 140, and magnet 150 is placed on the inner side from the inner diameter parts, via air gaps from the inner periphery parts. That is to say, the inner periphery parts of coil 170 are placed to oppose the outer periphery planes of different poles of magnet 150 at a certain distance.

Also, between side wall parts 142 and 143 of outer yoke 140, coil 170 has a square cylindrical shape formed by winding a coil wire around an axis to extend in a direction virtually perpendicular to yoke center part 141 of outer yoke 140, base plate 112 and shaft 125.

This coil 170 is attached on inner wall planes of outer yoke side wall parts 142 and 143 closer to yoke center part 141 and is placed in locations to face different magnetic poles of magnet 150 (magnetic pole planes 150a and 170b).

Magnet (permanent magnet) 170, which is placed on the inner side of coil 170 via air gaps, is a cuboid having magnetic pole planes 150a and 170b that are long in the direction in which outer yoke 1504 extends. Here, magnet 150 is held in a rotatable fashion in an air gap on the inner side of coil 170, by means of magnet holding part 124F held rotatably by support wall parts 114A and 116A via elastic members 130.

This magnet holding part 124F is formed in the shape of a letter C placed sideways on a side view, and has bottom plate part 124a of a flat rectangular shape on which magnet 150 is placed, and front wall part 124b and rear wall part 124c that that erect from edge parts of bottom plate part 124a that are spaced apart along the long direction (that is, along the direction in which shaft 125 extends).

This magnet holding part 124F is formed of a non-magnetic body. In front wall part 124b, shaft 125 is attached perpendicular, and, in rear wall part124c, shaft 126 is placed to be positioned coaxially with shaft 125. That is to say, shaft 125 is placed approximately along the center of magnet 150, approximately parallel to varying magnetic pole planes 150a and 150b of magnet 150 (see FIG. 19).

Magnet holding part 124F places magnet 150 apart from coil 170 and the back of yoke center part 141 of outer yoke 140, and holds magnet 150 to be able to rotate in twisting direction about the axis of shafts 125 and 126. In movable body 120F, coil 170 is placed between front wall part 124b of magnet holding part 124F and magnet 150 and between rear wall part 124c and magnet 150, without making coil 170 touch these wall parts or magnet 150, so that movable body 120F is able to move on the inner side and outer side of coil 170.

Magnetic pole planes 150a and 150b of magnet 150, held by magnet holding part 124F, are placed to oppose, entirely, the inner wall planes of outer yoke sidewall parts 142 and 143 via coil 170.

Here, the S-pole end (S magnetic pole plane 150a) of magnet 150 faces the inner wall plane 142a of sidewall part 142 of outer yoke 140, and the N-pole side (N magnetic pole plane 150b) faces the inner wall plane 143a of sidewall part 143 of outer yoke 140.

Incidentally, as shown in FIG. 16 and FIG. 17, shaft 125 is provided to project outward from support wall part 116A in the same direction as the direction of extension of outer yoke 140. That is to say, in actuator 100F, shaft 125 is provided to project in a direction that is virtually perpendicular to the direction magnet 150 and side wall parts 142 and 143 oppose each other over coil 170.

Shaft 125 is fixed in front wall part 124b of magnet holding part 124F in this way, and, by this means, is attached to movable body 120F to be located on an axis to pass the center of gravity of movable body 120F. By this means shaft 125 is able to move in back-and-forth rotating vibration with magnet 150 and magnet holding part 124F constituting the main body of movable body 120F, and transmit this vibration outside.

When actuator 100F is used for an electric toothbrush, a toothbrush part is coaxially coupled with shaft 125, and, at the head of this toothbrush part, a hair bundle part is provided to be perpendicular to the axial direction. By this means the toothbrush part moves in the same motion as shaft 125, that is, moves in rolling motion, which is back-and-forth rotating vibration.

With actuator 100F of the present embodiment, assuming that the inertia of movable body 120F is J and the spring constant in a twisting direction is $k_{sp}$, as compared with fixed body 110F, movable body 120F vibrates in a resonance frequency calculated based on equation 1 below:

(Equation 1)

$$f_0 = \frac{1}{2\pi}\sqrt{\frac{K_{sp}}{J}} \qquad [4]$$

In actuator 100F of the present embodiment, an alternating current of substantially the same frequency as a resonance frequency $f_0$ of movable body 120F is supplied from alternating current supplying part 180 to coil 170. By this means, it is possible to drive movable body 120F efficiently.

As shown in FIG. 18, in fixed body 110F and movable body 120F, outer yoke 140, magnet 150 and coil 170 form a magnetic circuit.

To be more specific, actuator 100 has a magnetic circuit where magnetic fluxes produced from magnet 150 (designated by outline arrows) pass an air gap where coil 170 is placed, sidewall part 143 of outer yoke 140, yoke center part 141, sidewall part 142 and the opposite air gap, in order, and reaches the opposite pole of magnet 150.

Movable body 120F of this actuator 100F is supported by a spring mass system structure supported by fixed body 110F via elastic members 130 (see FIG. 16 and FIG. 17). When an alternating current of the same frequency as resonance frequency $f_0$ of movable body 120F is supplied to coil 170, movable body 120F is driven in a resonant state. The back-and-forth rotating vibration that is produced then is transmitted to shaft 125 of movable body 120F.

Actuator 100F is driven based on the equation of motion represented by equation 2 below and based on the circuit equation represented by equation 3 below.

(Equation 2)

$$J\frac{d^2\theta(t)}{dt^2} = K_t i(t) - K_{sp}\theta(t) - D\frac{d\theta(t)}{dt} - T_{Load} \qquad [5]$$

J: Inertia moment [Kgm2]
θ(t): Angle [rad]
$K_t$: Torque constant [Nm/A]
i(t): Current [A]
$K_{sp}$: Spring constant [Nm/rad]
D: Attenuation coefficient [Nm/(rad/s)]
$T_{LOAD}$: Load torque [Nm]

(Equation 3)

$$e(t) = Ri(t) + L\frac{di(t)}{dt} + K_e\frac{d\theta(t)}{dt} \qquad [6]$$

e(t): Voltage [V]
R: Resistance [Ω]
L: Inductance [H]
$K_e$: Counter electromotive force multiplier [V/(rad/s)]

That is to say, the inertia moment, rotation angle, torque constant, current, spring constant, attenuation coefficient, and load torque in actuator 100F can be changed as adequate in a range to satisfy equation 2, and the voltage, resistance, inductance, and counter electromotive force multiplier can be changed as adequate in a range to satisfy equation 3.

Next, the operations of actuator 100F will be described in detail.

FIG. 19 is a schematic view for explaining operation of actuator 100F according top the seventh embodiment. Although the flow of magnetic fluxes from magnet 150 is shown by outline arrows in FIG. 19A, the same flow applies to FIG. 19B to FIG. 19D, and illustration is omitted in FIG. 19B to FIG. 19D. Also, although FIG. 19A shows alternating current supplying part 180 that supplies an AC voltage to coil 170, the same applies to FIG. 19B to FIG. 19D, and illustration is omitted in FIG. 19B to FIG. 19D.

When an alternating current is supplied from alternating current supplying part 180 to coil 170, thrusts F1, F2, F3 and F4 are produced in coil 170, following Fleming's left hand rule. By this means, in movable body 120F that is attached to base plate 112 and support wall parts 114A and 116A via elastic members 130 in a movable fashion, a rotating force about an axial center at the center of rotation is produced.

One operation cycle of actuator 100F will be described.

When a current flows in coil 170 in the direction shown in FIG. 19A (a current to flow in this direction will be hereinafter referred to as "forward current"), downward thrust F1 (directed toward base plate 112) is produced in part 170b of coil 170 opposing N-pole plane 150b of magnet 150. Meanwhile, in part 170a of coil 170 opposing S pole plane 150a of magnet 150, upward thrust F2 (directed toward yoke center part 141 of outer yoke 140) is produced.

By this means, a rotating force is produced in movable body 120F that has magnet 150 and that is supported by support wall parts 114 and 116 that erect from base plate 112 of fixed body 110F (see FIG. 2 and FIG. 3), via elastic members 130. In movable body 120F, thrusts R1 and R2 work on magnet 150 as reaction forces to thrusts F1 and F2 of coil 170. By this means, movable body 120F moves anticlockwise to assume the position shown in FIG. 19B.

With actuator 100F shown in FIG. 19B, a reaction force to place movable body 120F in the state of FIG. 19A by the restoring force of elastic members 130 (see FIG. 17 and FIG. 18), is produced. From the state shown in FIG. 19B to the state shown in FIG. 19D, a reverse current is supplied to coil 170 as compared with FIG. 19A. By this means, from the state shown in FIG. 19B to the state shown in FIG. 19C, movable body 120F rotates anticlockwise with respect to fixed body 110F, by the reaction force of elastic members 130 and thrusts R3 and R4 produced as reaction forces to the thrusts designated by arrows F3 and F4. From the state shown in FIG. 19C to the state shown in FIG. 19D, movable body 120F rotates anticlockwise with respect to fixed body 110F by the thrusts that work upon magnet 150, designated by arrows F3 and F4.

With actuator 100F shown in FIG. 19D, a reaction force to place movable body 120F in the state of FIG. 19A by the restoring force of elastic members 130 is produced. From the state shown in FIG. 19D, passing the state shown in FIG. 19A, to the state shown in FIG. 19B, a forward current is supplied to coil 170. By this means, from the state shown in FIG. 19D to the state shown in FIG. 19A, movable body 120F rotates anticlockwise with respect to fixed body 110F, by the reaction force of elastic members 130 and by thrusts R1 and R2 which are produced as reaction forces to the thrusts designated by arrows F1 and F2 and which work upon magnet 150.

From the state shown in FIG. 19A to the state shown in FIG. 19B, movable body 120F rotates anticlockwise with respect to fixed body 110F by the thrusts designated by arrows R1 and R2. Although movable body 120F moves in back-and-forth rotating motion, on the inner side of coil 170, approximately about the extending center axis of magnet 150, it is equally possible to operate movable body 120F in the same way as shown in FIG. 19, by thrusts R1 to R4, without using the reaction force of magnetic member 130.

Next, what alternating current is supplied to coil 170 of movable body 120F in each state shown in FIG. 19 will be described briefly.

The alternating current to flow in the coil may be a pulse wave of frequency $f_0$ as shown in FIG. 6A or may be a sine wave of frequency $f_0$ as shown in FIG. 6B.

In the state of FIG. 19A, the forward current at time point t1 shown in FIG. 6 is supplied. In the state of FIG. 19B, the direction of the current is switched as shown at time point t2 in FIG. 6. In the state of FIG. 19C, the reverse current at time point t3 shown in FIG. 6 is supplied. Also, in the state of FIG. 19D, the direction of the current is switched as shown at time point t4 in FIG. 6, and, in the state of FIG. 19D, the forward current at time point t5 shown in FIG. 6 is supplied. This is one operation cycle, and, by repeating these operations, movable body 120F repeats the displacement operations shown in FIG. 19A to FIG. 19D, and, by this means, produces back-and-forth rotating vibration.

In actuator 100F, movable body 120F produces back-and-forth rotating motion (that is, back-and-forth rotating vibration), and this back-and-forth rotating vibration is sent outside via shaft 125. When a toothbrush part is coupled with shaft 125 and a hair bundle part is provided to be perpendicular to the axial direction at the head of this toothbrush part, the toothbrush part moves in back-and-forth rotating vibration and makes possible rolling brushing.

By this means, actuator 100F satisfies equations 2 and 3 and is driven by a resonance phenomenon using the resonance frequency represented by equation 1. By this means, in actuator 100F, the power to be consumed in a static state by resonance drive is only the loss due to load torque and the loss due to friction and the like, so that low power drive is possible—that is, it is possible to move movable body 120F in back-and-forth rotating vibration at low power consumption. As described above, with actuator 100F of the present embodiment, it is possible to realize back-and-forth rotating motion of an electric toothbrush or the like without using a drive transmitting mechanism apart from a drive source, and furthermore make possible back-and-forth rotating motion at low power consumption.

Furthermore, movable body 120F is formed with magnet 150 and magnet holding part 124F, without using large-sized components like outer yoke 140. Consequently, the scale of the inertia moment of movable body 120F does not depend on the outer shape and can be determined based upon the shape of magnet 150. Furthermore, given that magnet 150 is placed such that its center of gravity is located near shaft 125, which is the output shaft of movable body 120F, and, to be more specific, approximately on the axis of shaft 125, so that magnet 150 is unlikely to be a factor to increase the inertia. The increase of inertia moment due to change of the outer shape of actuator 100F is reduced, so that constraints are removed in terms of design, and it is therefore possible to improve the freedom of design with respect to actuator 100F itself.

An electric toothbrush having actuator 100F provides the same advantage, so that it is possible to miniaturize the electric toothbrush itself.

Also, although with the configuration of actuator 100F according to the seventh embodiment base plate 112 is a non-magnetic body, this is by no means limiting, and it is equally possible to use a magnetic body. This configuration will be explained now with reference to FIG. 20.

(Eighth Embodiment)

Figure 20:
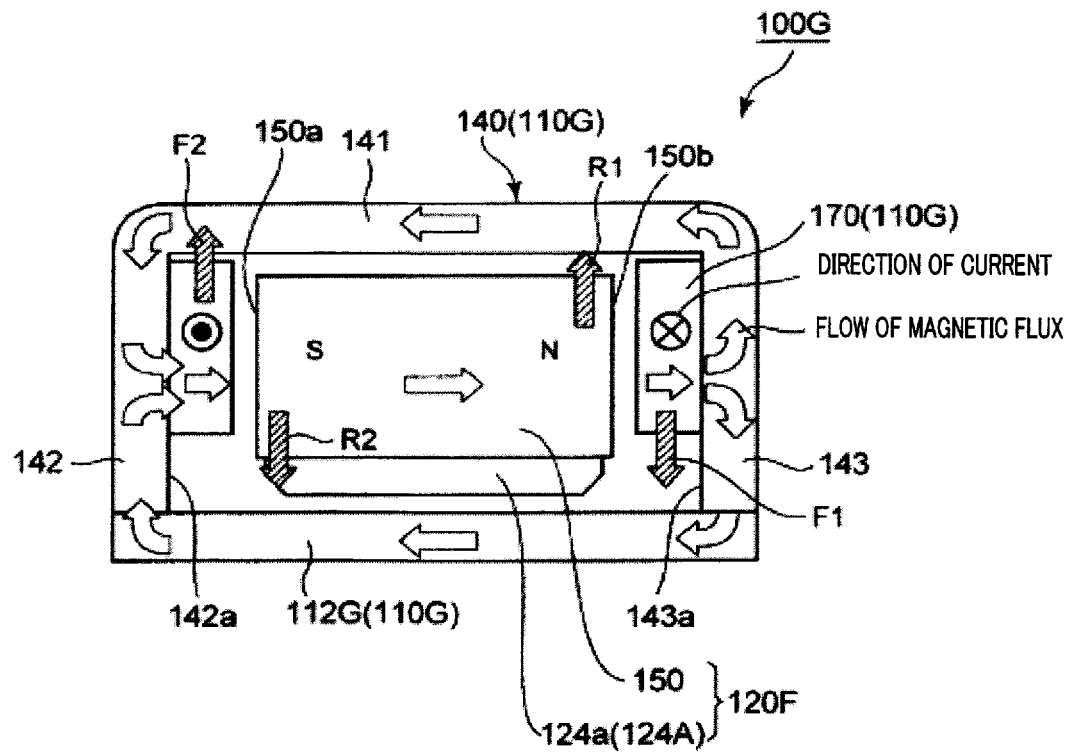
FIG. 20 is a schematic cross-sectional view showing a principal-part configuration of an actuator according to an eighth embodiment of the present invention.

FIG. 20 is a schematic cross-sectional view showing a principal-part configuration of an actuator according to an eighth embodiment of the present invention. FIG. 20 shows the flow of magnetic fluxes, from magnet 150 as a magnetic circuit of actuator 100F, with outline arrows.

Actuator 100G shown in FIG. 20 replaces non-magnetic base plate 112 in the configuration of actuator 100F with magnetic base plate 112G. Consequently, the other parts of actuator 100G are the same as in actuator 100F, and their detailed descriptions will be omitted.

Fixed body 110G of actuator 100G has coil 170 that is placed to surround the periphery of magnet 150 of movable body 120F via an air gap, outer yoke 140, which is a magnetic body to fix the outer periphery parts of coil 170 to opposing inner wall planes 142*a* and 143*a*, and base plate 11G, which is a magnetic body.

That is to say, with actuator 100G, magnet 150 and magnet holding part 124F of movable body 120F (only bottom plate part 124*a* is shown in FIG. 20) are surrounded by outer yoke 140 and base plate 112G, which are magnetic bodies. Magnet 150 is placed on the inner side of base plate 112G and on the inner side of coil 170 such that, similar to the configuration of actuator 100F, magnetic pole planes 150*a* and 150*b* are directed toward sidewall parts 142 and 143 of outer yoke 140, at a certain distance, in a direction perpendicular to the direction coil 170 is wound.

With this configuration, compared to actuator 100F, actuator 100G forms two paths for magnetic fluxes by magnet 150 in fixed body 110G.

That is to say, as shown in FIG. 20, in the magnetic circuit of actuator 100G, magnetic fluxes (shown by outline arrows) that are produced from magnet 150 reach sidewall part 143 of outer yoke 140, from magnetic pole plane 150*b*, passing an air gap where coil 170 is placed. Next, from sidewall part 143, the magnetic fluxes pass both yoke center part 141 and base plate 112G on the opposite side from yoke center part 141, and then arrive at sidewall part 143. Magnetic fluxes pass sidewall part 142 and the opposite air gap in order, and continue to the opposite pole of magnet 150 (magnetic pole plane 150*a*). The operation of movable body 120 in actuator 100G is virtually the same as in actuator 100F, and so descriptions will be omitted here. FIG. 20 shows thrusts F1 and F2 that are produced when a forward current is applied, and thrusts R1 and R2 of magnet 150, which are reaction forces to these. When thrusts R1 and R2 are produced, movable body 120F moves in the directions of thrusts R1 and R2. When the direction of current changes, reverse thrusts to F1 and F2 work on coil 170, and, by this means, opposite thrusts to R1 and R2 work on magnet 150, and, consequently, movable body 120F moves in directions designated by reverse thrusts to R1 and R2. By repeating these, similar to the seventh embodiment, actuator 100G moves mobile body 120F in back-and-forth rotating vibration.

As described above, with actuator 100G of this eight embodiment, it is possible to achieve similar or the same working effects as actuator 100F such as realizing back-and-forth rotating motion of an electric toothbrush or the like without using a drive transmitting mechanism apart from a drive source. In addition, with actuator 100G, the magnetic saturation in the magnetic circuit is reduced, so that it is possible to increase the thrust of movable body 120F that is produced when an AC voltage is supplied from alternating current supplying part 180 to coil 170.

Compared to the configuration of actuator 100F according to the seventh embodiment, actuator 100G is able to increase the torque which coil 170 produces to move movable body 120F by 1.25 times.

Furthermore, with this second embodiment, the outer periphery part of fixed body 110F accommodating movable body 120F in a movable fashion—that is, a magnetic circuit—is formed with outer yoke 140, which is a magnetic body, and base plate 112G, which is a magnetic body.

That is to say, by forming the outer surface of actuator 100G using a magnetic body, in actuator 100G, it is possible to prevent magnetic fluxes from leaking from the magnetic circuit including base plate 112G, outer yoke 140, magnet 150 and coil 170.

(Ninth Embodiment)

To briefly summarize an actuator according to a ninth embodiment, based upon the configuration of actuator 100F (see FIG. 17 and FIG. 18), coil 170 is removed from outer yoke 140, fixed on base plate 112 via a non-magnetic body (spacer), and movable body 120F is turned upside down and fixed on fixed body 110F to be able to move in twisting directions in back-and-forth rotating vibration via non-magnetic members 130.

Figure 21:
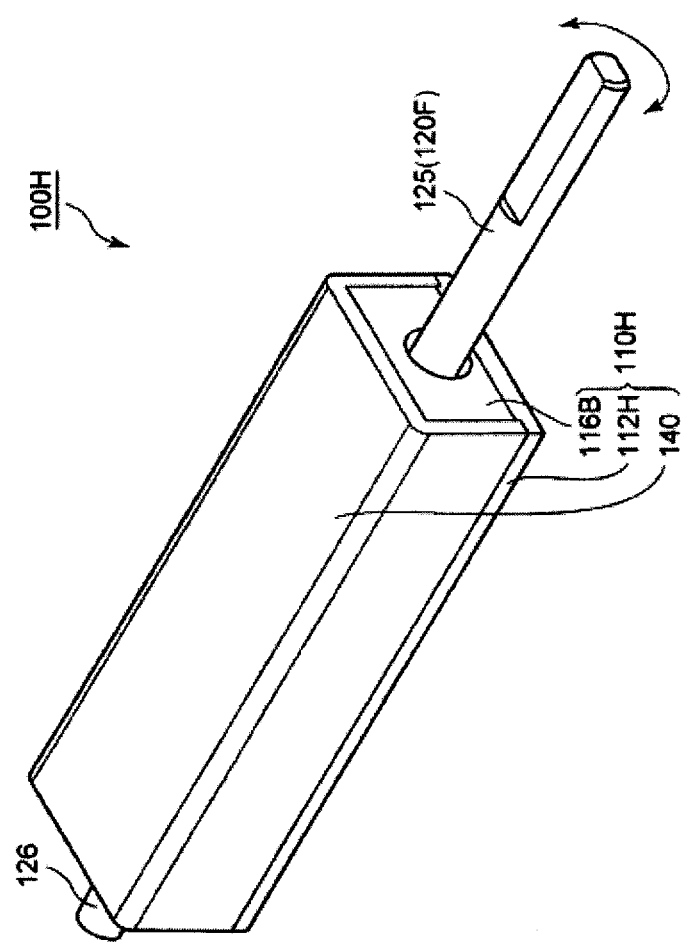
FIG. 21 is an outer view of a configuration of an actuator according to a ninth embodiment of the present invention.
Figure 22:
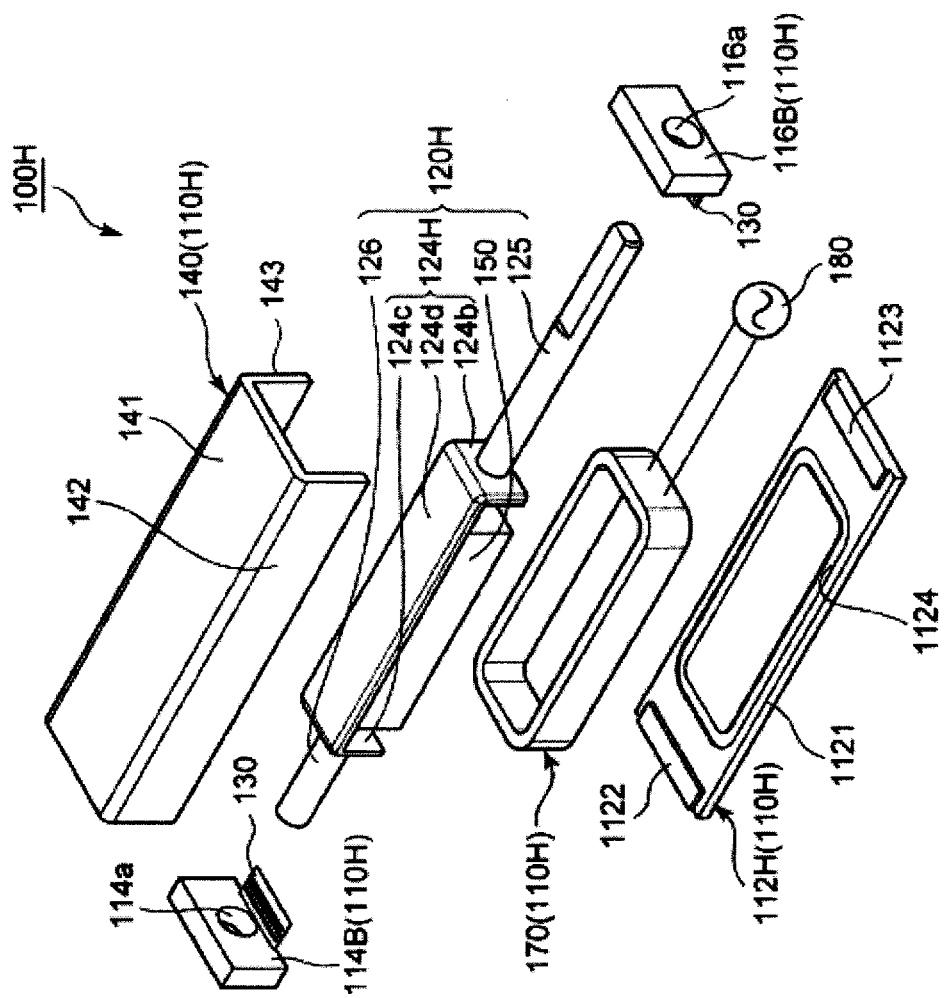
FIG. 22 is an exploded perspective view showing an actuator according to the ninth embodiment of the present invention.
Figure 23:
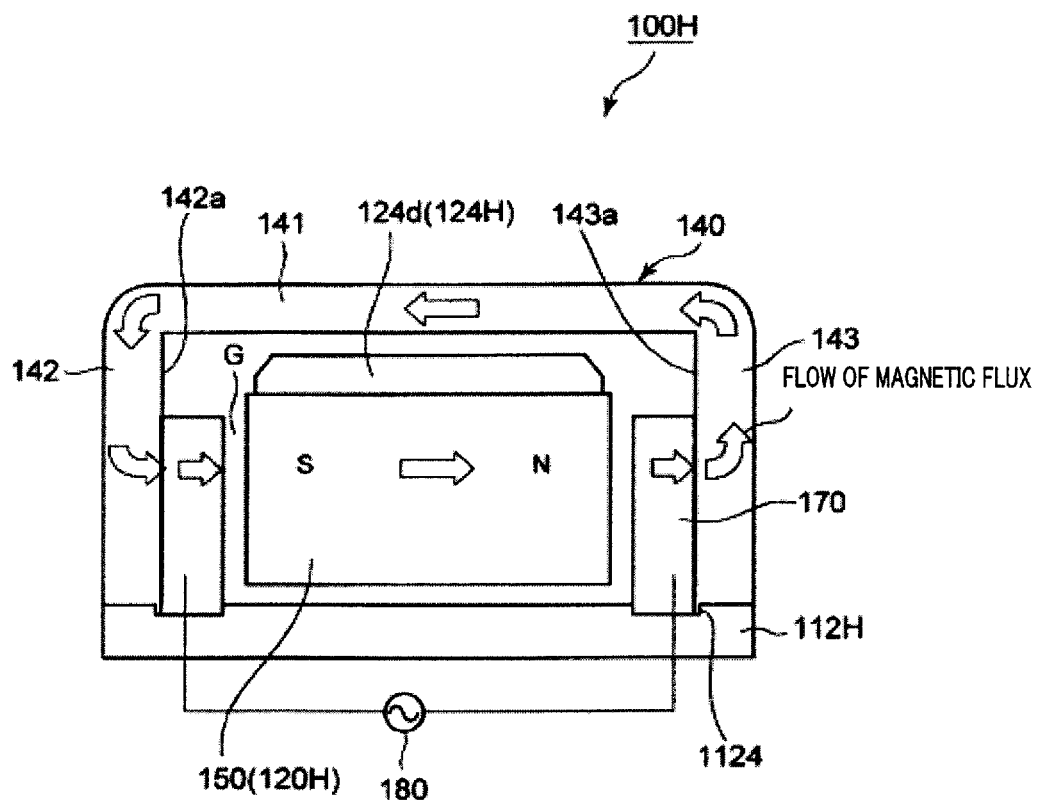
FIG. 23 is a schematic cross-sectional view showing a principal-part configuration of an actuator according to the ninth embodiment of the present invention.

FIG. 21 is an outer view of actuator 100H according to a ninth embodiment of the present invention, FIG. 22 is an exploded perspective view of this actuator 100H, and FIG. 23 is a schematic cross-sectional view showing a principal-part configuration of this actuator 100H. This actuator 100H basically has the same configuration as actuator 100F according to the seventh embodiment, shown in FIG. 16, and therefore parts in actuator 100H that are the same as in actuator 100F will be assigned the same reference numerals and codes as in actuator 100F and their explanations will be omitted.

As shown in FIG. 21 to FIG. 23, actuator 100H has fixed body 110H that has outer yoke 140, base plate 112H, coil 170 and support wall parts 114B and 116B, movable body 120H that has magnet 150 placed on the inner side (the inner periphery part) of coil 170 via an air gap, elastic members 130 that support movable body 120H on fixed body 110H such that movable body 120H is able to rotate back and forth in twisting directions about shaft 125 of movable body 120H, and alternating current supplying part 180 (see FIG. 22 and FIG. 23).

In fixed body 110H, base plate 112H has base plate main body 1121 formed of a non-magnetic body of a flat rectangular shape. At edge parts on the surface of this base plate main body 1121, that are spaced apart along the long direction, positioning projection parts 1122, and 1123 that project upward and that fit in recesses formed in the lower planes of support wall parts 114B and 116B are provided. Support wall parts 114B and 116B are provided to erect from the places in base plate main body 1121 where support wall parts 114B and 116B are positioned via positioning projection parts 1122 and 1123.

Furthermore, in the center area on the surface of base plate main body 1121, annular fitting channel part 1124 is formed. This annular fitting channel part 1124 is formed to match the shape of coil 170, has an inner diameter to match the inner diameter of the cylindrical part of coil 170, and provides a channel having a slightly greater width that the thickness of the cylindrical part of coil 170. Coil 170 is provided to be positioned in annular fitting channel part 1124.

Base plate 112H is provided such that outer yoke 140 having a U-shaped cross section covers the surface of base plate 112H and support wall parts 114B and 116B from above in a state in which sidewall parts 142 and 143 contact the outer periphery part of coil 170 on base plate 112H.

On the inner side of coil 170 provided in base plate 112H— that is, in the inner part—magnet 150 provided via an air gap.

In the area surrounded by outer yoke 140 and base plate 112H, magnet 150 is held by magnet holding part 124H supported in a rotatable fashion on the inner side of coil 170, via elastic members 130 in support wall parts 114B and 116B.

Magnet 150 is held by magnet holding part 124H in a location apart from base plate 112H and yoke center part 141 such that different magnetic pole planes 150*a* and 150*b* of magnet 150 face coil 170 via an air gap.

Magnet holding part 124H has upper plane part 124*d* that is fixed on the upper plane of magnet 150, and front wall part 124*b* and rear wall part 124*c* that hang from edge parts of upper plane part 124*d* (front and rear edge parts) that are spaced part in the long direction of upper plane part 124*d*. Magnet holding part 124H is provided perpendicular to front wall part 124*b* and rear wall part 124*c* and inserts shafts 125 and 126, which are provided along the position of the center of gravity of magnet 150, in opening parts 114a and 116a of support wall parts 114B and 116B of fixed body 110H. Furthermore, magnet holding part 124H is provided in support wall parts 114B and 116B to be able to move via elastic members 130. By this means, magnet 150 and magnet holding part 124H are provided on the inner side of coil 170 placed in the periphery of magnet 150 so as to be capable of back-and-forth rotation in twisting directions about shafts 125 and 126. Similar to the seventh embodiment, elastic members 130 are provided in support wall parts 114B and 116B. To be more specific, elastic members 130 are provided in inner lower side parts of support wall parts 114B and 116B (formed similar to support wall parts 114A and 116A), integrally, by means of insert molding.

Similar to actuator 100F of the seventh embodiment and actuator 100G of the eighth embodiment, an alternating current having approximately the same frequency as a resonance frequency is supplied to coil 170 from alternating current supplying part 180 that supplies an AC voltage. By this means, mobile body 120H that is supported on fixed body 110H by elastic members 130 to be able to move in twisting directions of shaft 125, moves in back-and-forth rotation vibration, in fixed body 110H, by a reaction force that is produced in magnet 150 by the thrusts of coil 170.

FIG. 24 is schematic diagram showing operation of actuator 100H according to the ninth embodiment of the present invention. Although the flow of magnetic fluxes from magnet 150 is shown by outline arrows in FIG. 24A, the same flow applies to FIG. 24B to FIG. 24D, and illustration is omitted in FIG. 24B to FIG. 24D. Furthermore, FIG. 24A illustrates alternating current supplying part 180 that supplies an AC voltage to coil 170, and, although the same flow of magnetic fluxes as in FIG. 24A is produced in FIG. 24B to FIG. 24D, this is not illustrated for ease of explanation.

As shown in FIG. 24A, in actuator 100H, a magnetic circuit is formed in which magnetic fluxes produced from magnet 150 (designated by outline arrows) pass, from magnetic pole plane 150b, air gap G, coil 170, side wall parts 143 of outer yoke 140, yoke center part 141, side wall parts 142, an the opposite air gap, in order, and reach the opposite pole of magnet 150 (magnetic pole plane 150a).

In actuator 100H, when an alternating current is supplied from alternating current supplying part 180 to coil 170, thrusts designated by arrows F1, F2, F3 and F4 in the drawing are produced in coil 170, following Fleming's left hand rule. In response to this, rotating forces (thrusts R1 to R4) about an axial center being shaft 125, which is the center of rotation, are produced in magnet 150, and, similar to the case of mobile body 120F of actuator 100F shown in FIG. 19, movable body 120F repeats the operations of FIG. 24A, FIG. 24B, FIG. 24C, and FIG. 24D, and produces back-and-forth rotating vibration.

Actuator 100H thus has the same working effects as actuator 100F. In addition, with this actuator 100H, upon assembly, coil 170 is attached to base plate 112H. Furthermore, upon assembly, coil 170 is placed on the surface of flat base plate 112H, so that, compared to the case of placing coil 170 in the denting interior of U-shaped outer yoke 140, it is possible to perform installation easily.

In this case, coil 170 is attached to be positioned in annular fitting channel part 1124 formed on the surface of base plate 112H, so that it is possible to install coil 170 in a location positioned in base plate 112H.

Generally, coil 170 is made by winding a coil wire around a jig that defines the inner diameter of the coil, it is difficult to accurately control the outer diameter dimension of resulting coil 170. Consequently, when coil 170 is provided inside outer yoke 140, it is necessary to attach the outer periphery part of coil 170 to outer yoke 140, so that accurate control is required upon making of coil 170 and this is burdensome.

By contrast with this, with the present embodiment, in base plate 112H, coil 170 is directly placed in annular fitting channel part 1124 where the inner diameter is defined, it is possible to determine the position of installation by the inner periphery part of coil 170. Consequently, with actuator 100H, it is possible to improve the assembly and reduce the work load.

Although, actuator 100H places, for example, coil 170 differently compared to actuator 100F, the magnetic circuit configuration is the same, and it is therefore possible to achieve the same working effects as by actuator 100F of the seventh embodiment. Especially, with actuator 100H of the present embodiment, it is possible to realize back-and-forth rotating motion of an electric toothbrush or the like without using a drive transmitting mechanism apart from a drive source.

Also, although with the configuration of actuator 100H base plate 112H is a non-magnetic body, this is by no means limiting, and it is equally possible to make base plate 112H a magnetic body. In this case, similar to the eighth embodiment, the path of magnetic fluxes in fixed body 110H passes, from one side wall part 143, yoke center part 141 and base plate 112H, in order, and reaches side wall part 142 on the other side, and therefore it is possible to provide the same advantage as by the second embodiment.

(Tenth Embodiment)

Figure 25:
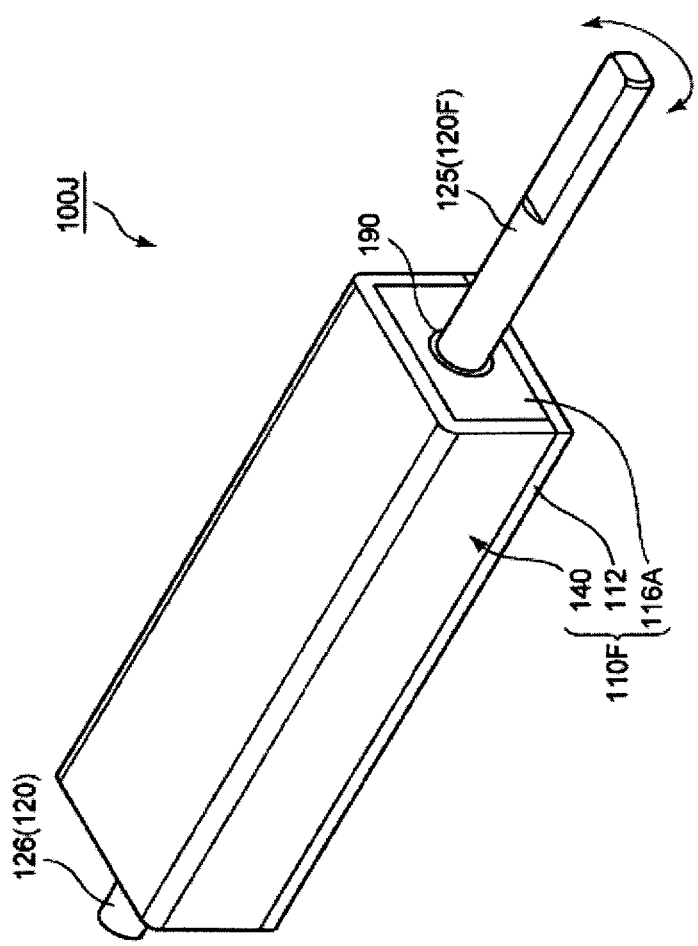
FIG. 25 is a perspective view showing an actuator according to a tenth embodiment of the present invention.
Figure 26:
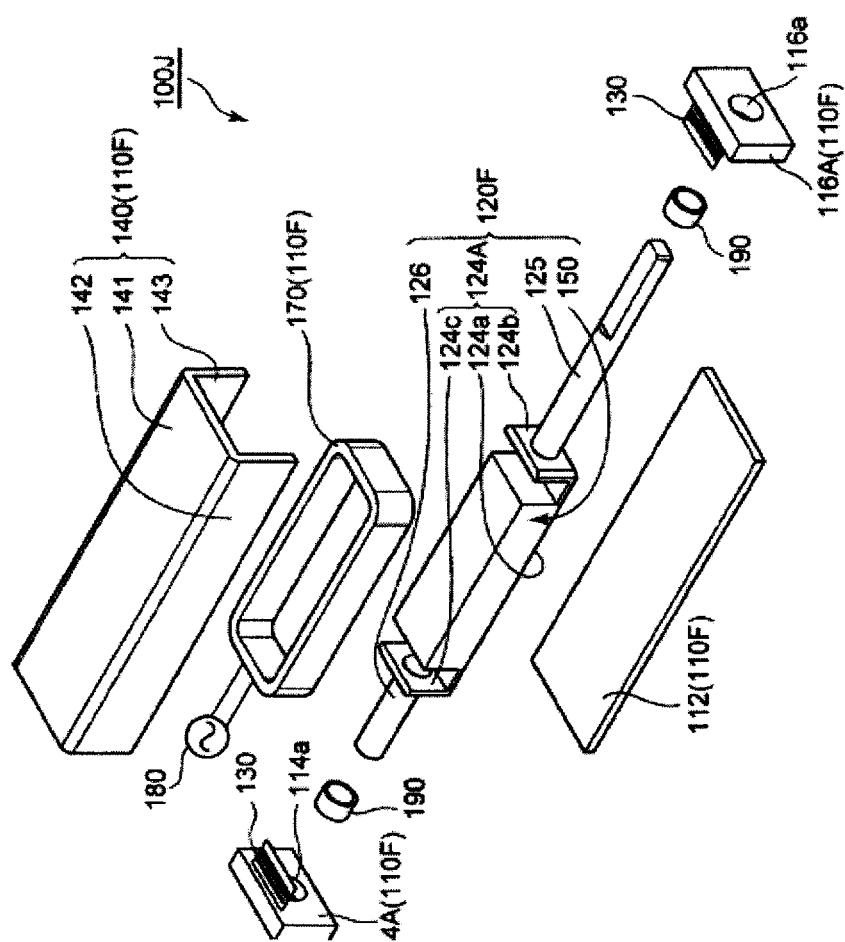
FIG. 26 is a principal-part exploded perspective view of an actuator according to the tenth embodiment of the present invention.

FIG. 25 is a perspective view showing actuator 100J according to a tenth embodiment of the present invention, and FIG. 26 is a principal-part exploded perspective view of this actuator 100J. This actuator 100J basically has the same configuration as actuator 100F according to the seventh embodiment, shown in FIG. 16, and therefore parts in actuator 100J that are the same as in actuator 100F will be assigned the same reference numerals and codes as in actuator 100F and their explanations will be omitted.

Based upon actuator 100F shown in FIG. 16, actuator 100J according to the tenth embodiment has a configuration in which shafts 125 and 126 are inserted through support wall parts 114A and 116A of fixed body 110F via bearing 190 and axially supported in a rotatable fashion, and the rest of the configurations are the same.

That is to say, as shown in FIG. 25 and FIG. 26, in actuator 100J, shaft 125 which movable body 120F has is rotatably inserted in bearing 190 attached to opening part 116a of support wall part 116A. This shaft 125 transmits and outputs the movement/motion of movable body 120F, and functions as a bearing to axially support movable body 120F on fixed body 110F.

Furthermore, shaft 126 that is placed coaxially with shaft 125 in movable body 120F and that projects in the opposite direction from shaft 125 is rotatably inserted in bearing 190 attached to opening part 114a of support wall part 114A.

Consequently, with actuator 100J, when an alternating current is supplied from alternating current supplying part 180 to coil 170, movable body 120F having coil 170 moves in stable back-and-forth rotating vibration about an axial center of shaft 125 with respect to fixed body 110F.

In this way, with actuator 100J, movable body 120F is axially supported by support wall parts 114A and 116A, via shafts 125 and 126 inserted in bearing 190, in a rotatable fashion, with freedom in the rotating direction and axial direction. Furthermore, in a state in which movement in the axial direction is constrained, movable body 120F is supported by support wall parts 114A and 116A via elastic members 130. That is to say, movable body 120F uses an axial support structure using support wall parts 114A and 116A, shafts 125 and 126 and bearing 190, and is supported in fixed body 110F by securing freedom in the direction of rotation, so that movable body 120F is structured to be strong against shock.

Consequently, actuator 100J is able to achieve the same advantages as by actuator 100F, and, in addition, move in stable back-and-forth rotating motion by fixing the axis of rotation of shafts 125 and 126, so that it is possible to improve the robustness of the actuator itself against shock.

Although with this embodiment bearing 190 is provided in support wall parts 114A and 116A in actuator 100F according to the seventh embodiment to support shafts 125 and 126 of movable body 120F in a rotatable fashion, this is by no means limiting, and, for example, it is equally possible to provide bearing 190 in support wall parts 114A, 114B, 116A and 116B of actuator 100G and actuator 100H of the eighth and ninth embodiments and support shafts 125 and 126 of movable body 120F in a rotatable fashion.

(Eleventh Embodiment)

Figure 27:
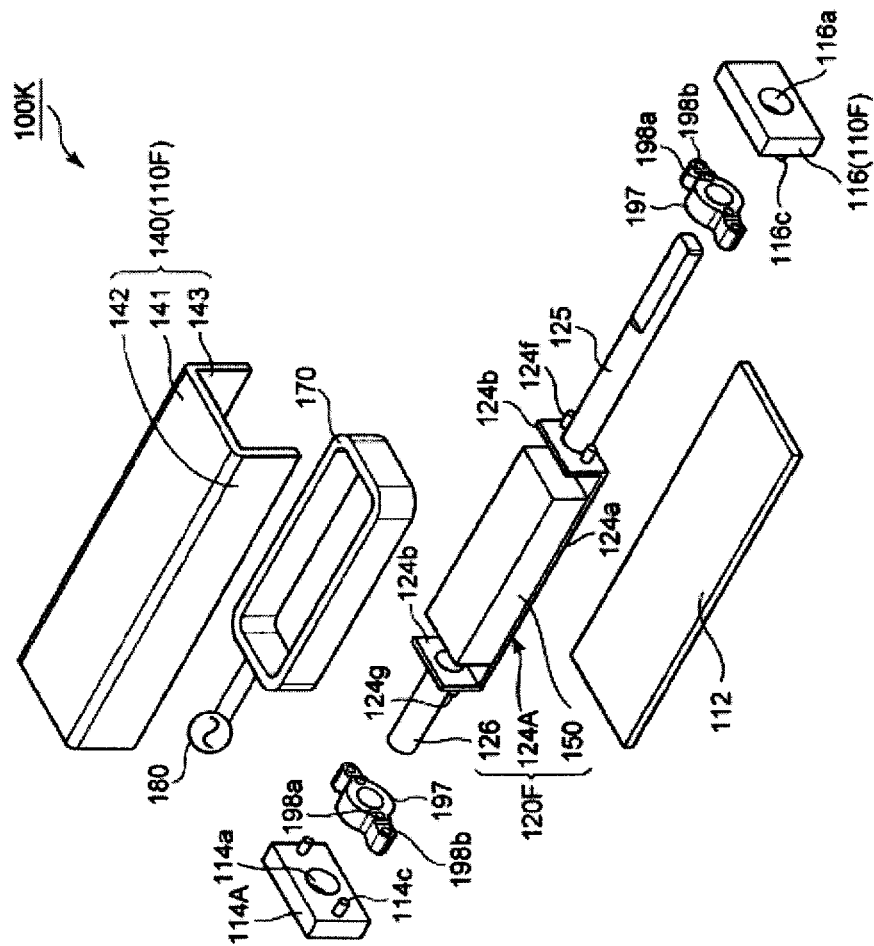
FIG. 27 is an exploded perspective view showing an actuator according to an eleventh embodiment of the present invention.

FIG. 27 is an exploded perspective view showing actuator 100K according to an eleventh embodiment of the present invention. Based upon actuator 100F according the seventh embodiment shown in FIG. 16 to FIG. 19, actuator 100K shown in FIG. 27 replaces the configuration of elastic members 130, and the rest of the configurations are the same. The same parts will be assigned the same reference numerals and codes and their explanations will be omitted.

Based upon the configuration of actuator 100F, with actuator 100K, a viscoelastic body which itself attenuates significantly (here, elastomer 197 for actuator 200E according to the sixth embodiment, as shown in FIG. 15) is used instead of elastic members 130 (which are zigzag springs).

Elastomer 197 (see FIG. 27 and FIG. 15) is the same as that of the sixth embodiment, and, placed between support wall parts 116A and 114A and front wall part 124b and rear wall part124c of coil holding part 124F, functions as a spring. In elastomer 197, projections 114c, 116c, 124f and 124g formed in support walls parts 116A and 114A and rear wall parts 124b and 124c are inserted and fit in holes 198a and 198b formed in locations shifted in the direction arm part 197b extends.

Here, in arm parts 197b of elastomer 197, projections 124f and 124g of front and rear wall parts 124b and 124c are pressed and fit in holes 198a in locations near center part 197a. Furthermore, projections 116c and 114c of support wall parts 116A and 114A are pressed and fit in holes 198b in locations father from center part 197a.

Actuator 100K thus has characteristics of the seventh embodiment and provides the same working advantages as by actuator 100F. In addition, by placing elastomer 197 between support wall parts 116A and 114A and front wall part 124b and rear wall part 124c of magnet holding part 124F, and by pressing projections 114c, 116c, 124f and 124g of support wall parts 116A and 114A, front wall part 124b and rear wall part 124c, into holes 198a and 198b, actuator 100K can be attached to both members (that is, support wall parts and front and rear wall parts). By this means, unlike cases where metallic springs such as zigzag springs and flat springs are used, complex processes of installation such as fastening of screws, bonding and insert molding are not necessary, and it is possible to allow elastomer 197 to function as a spring only by sandwiching elastomer 197 between movable body 120F and fixed body 110F, and it is therefore possible to improve the assembly of actuator 100K itself.

Instead of elastic members 130 of actuators 100G and 100H, elastomer 197 for actuator 100K may support movable body 120F on fixed body 110F such that movable body 120F is able to move in twisting directions about the axis of shafts 125 and 126.

Various changes can be made to the present invention without departing from the spirit of the present invention, and such changes are certainly within the scope of the present invention.

The disclosures of Japanese Patent Application No. 2008-282360, filed on Oct. 31, 2008, and Japanese Patent Application No. 2008-282361, filed on Oct. 31, 2008, including the specifications, drawings, and abstracts, are incorporated herein by reference in their entirety.

INDUSTRIAL APPLICABILITY

An actuator according to the present invention provides an advantage of realizing back-and-forth rotating motion of an electric toothbrush or the like without using a drive transmitting mechanism apart from a drive source and allowing miniaturization of an electric toothbrush or the like, and therefore is suitable for use as an actuator that is used for an electric toothbrush or the like to produce back-and-forth rotating vibration.

REFERENCE SIGNS LIST 100, 100A, 100B, 100C, 100D, 100E, 100F, 100G, 100H, 100J, 100K
Actuator
110, 110A, 110B, 110C, 110F, 110G, 110H Fixed body
112, 112A, 112B, 112C, 112G, 112H Base plate
114, 116, 114A, 114B, 116A, 116B Support wall part
120, 120B, 120C, 120F, 120H Movable body
124, 124B Coil holding part
124F, 124H Magnet holding part
124b Front wall part
124c Rear wall part
125, 126 Shaft
130 Elastic member
140 Outer yoke
141 Yoke center part (center part)
142, 143 Sidewall part
142a, 143a Inner wall part
150 Magnet (permanent magnet)
150a, 150b Magnetic pole plane
160, 160C Non-magnetic body
160B Projection
170 Coil
180 Alternating current supplying part
190 Bearing
197 Elastomer

The invention claimed is:

1. An actuator comprising:
a permanent magnet that has magnetic pole planes of different poles;
an outer yoke that has inner wall planes opposing each other and facing the magnetic pole planes with a predetermined interval therebetween respectively;
a coil that is placed through the interval and surrounds the permanent magnet;
a movable body that has one of the permanent magnet or the coil;
a fixed body that has the other one of the permanent magnet or the coil, and the outer yoke, and supports the movable body in a movable fashion via an elastic support part; and
an alternating current supplying part that supplies an alternating current to the coil, alternating current having a frequency substantially the same as a resonance frequency of the movable body,
wherein the movable body has an output shaft that is substantially parallel to the different magnetic pole planes of the permanent magnet and placed approximately at a center of the permanent magnet, and is supported by the elastic member part in such a way that the movable body moves in a twisting direction about the output shaft.

2. The actuator according to claim 1, wherein the movable body has the coil, and the fixed body has the permanent magnet.

3. The actuator according to claim 2, wherein the permanent magnet is attached to the outer yoke via a non-magnetic body.

4. The actuator according to claim 2, wherein:
the outer yoke has a center part and sidewall parts to form a U-shaped cross section that is open downward;
the fixed body has a magnetic base plate above which the movable body is placed;
the outer yoke is attached to the base plate to cover the movable body; and
the sidewall parts are closed at respective bottom parts thereof by the base plate.

5. The actuator according to claim 4, wherein the permanent magnet is attached to the base plate via a non-magnetic spacer.

6. The actuator according to claim 2, wherein:
the fixed body has a non-magnetic base plate above which the movable body is placed;
the outer yoke has a U-shaped cross section that is open downward and is attached to the base plate to cover the movable body; and
the permanent magnet is attached to the base plate.

7. The actuator according to claim 1, wherein the movable body has the permanent magnet and the fixed body has the coil.

8. The actuator according to claim 7, wherein the coil is attached to each of the inner wall planes of the outer yoke at an outer periphery part thereof.

9. The actuator according to claim 7, wherein the fixed body covers the movable body in a movable fashion by a magnetic body including the outer yoke.

10. The actuator according to claim 7, wherein:
the outer yoke has a U-shaped cross section that is open downward;
the fixed body has a flat base plate that is spaced below the movable body;
the coil is attached to the base plate; and
the outer yoke is attached to the base plate to cover the coil and the movable body inside the coil.

11. The actuator according to claim 10, wherein the base plate is made of a magnetic body.

12. The actuator according to claim 10, wherein an annular fitting channel part, in which the coil is placed, is formed on a surface thereof.

13. The actuator according to claim 10, wherein the movable body is axially supported by the fixed body in such a way that the movable body is able to rotate about the output shaft.

14. The actuator according to claim 1, wherein the elastic support part is a viscoelastic body that is provided between the fixed body and the movable body and that can be deformed between the fixed body and the movable body.

15. An electric toothbrush comprising:
the actuator of claim 1; and
a toothbrush part that is coaxially coupled with the output shaft, and that is provided with bristles at a head of the toothbrush part, the bristles being perpendicular to an axial direction of the output shaft.

* * * * *